(12) United States Patent
Fiebig et al.

(10) Patent No.: US 8,263,090 B2
(45) Date of Patent: Sep. 11, 2012

(54) VARIANTS OF GROUP 1 ALLERGENS FROM POACEAE HAVING REDUCED ALLERGENICITY AND MAINTAINED T-CELL REACTIVITY

(75) Inventors: Helmut Fiebig, Schwarzenbek (DE); Martin Wald, Hamburg (DE); Andreas Nandy, Hamburg (DE); Helga Kahlert, Hamburg (DE); Bernahrd Weber, Hamburg (DE); Oliver Cromwell, Suesel-Fassendorf (DE)

(73) Assignee: Merck Patent GmbH, Darmstadt (DE)

( * ) Notice: Subject to any disclaimer, the term of this patent is extended or adjusted under 35 U.S.C. 154(b) by 535 days.

(21) Appl. No.: 11/572,370

(22) PCT Filed: Jul. 11, 2005

(86) PCT No.: PCT/EP2005/007481
§ 371 (c)(1),
(2), (4) Date: Jan. 19, 2007

(87) PCT Pub. No.: WO2006/008018
PCT Pub. Date: Jan. 26, 2006

(65) Prior Publication Data
US 2008/0267985 A1    Oct. 30, 2008

(30) Foreign Application Priority Data

Jul. 21, 2004 (DE) .......................... 10 2004 035 337

(51) Int. Cl.
| | |
|---|---|
| C07K 1/00 | (2006.01) |
| C07H 21/02 | (2006.01) |
| C12P 21/04 | (2006.01) |
| A61K 39/00 | (2006.01) |
| A61K 39/38 | (2006.01) |
| A61K 39/35 | (2006.01) |
| A61K 39/36 | (2006.01) |

(52) U.S. Cl. ................. 424/275.1; 424/184.1; 435/71.1; 435/71.2; 530/350; 536/23.1

(58) Field of Classification Search ........................ None
See application file for complete search history.

(56) References Cited

U.S. PATENT DOCUMENTS
2005/0074464 A1    4/2005    Deweerd et al.

FOREIGN PATENT DOCUMENTS
WO    WO 03/025009 A    3/2003

OTHER PUBLICATIONS

Bhalla et al (Expert Review of Vaccines 2(1), 75-84 (2003).*
de Weerd et al. Allergology Interanational (2003) 52: 183-190.*
Matthews et al American Journal of Botany 87 (1): 96-107, 2000.*
Pertsen A et al, Post-translational modifications influence IgE Reactifity to the major allergen phl p 1 of Timothy Grass Pollen, Clinical and Experimental Allergy, Journal of the British Society for Allergy and Clinical and Immunology, Mar. 1998, pp. 315-321.
Schramm G et al, Allergen Engineer: Variants of the Timothy Grass Pollen Allergen Phl p 5b With Reduced IgE-binding Capacity but Conserved T Cell Reactivity, Journal of Immunology, Williams and Wilkins Co, Feb. 15, 1999, pp. 2406-2414.
Takai T et al, Engineering of the Major House Dust Mite Allergen Der F2 for Allergen-Specific Immunotherapy, Nature Biotechnology, Nature Publishing Aug. 1997, pp. 754-758.
Smith A. M. et al., Reduction in IGE Binding to Allergen Variants Generated by Site-Directed Mutagenesis: Contribution of Disulfide Bonds to the Antigenic Sytructure of the Major Hous Dust Mite Allergen Der, Molecular Immunology, Elmsford, NY, 1996, pp. 399-405.

* cited by examiner

*Primary Examiner* — Oluwatosin Ogunbiyi
(74) *Attorney, Agent, or Firm* — Millen, White, Zelano, Branigan, P.C.

(57) ABSTRACT

The present invention relates to the preparation and use of variants of the group 1 allergens of the Poaceae (sweet grasses) which are characterised by reduced IgE reactivity compared with the known wild-type allergens and at the same time by substantially maintained reactivity with T-lymphocytes. These hypoallergenic allergen variants can be employed for the specific immunotherapy (hyposensitisation) of patients having grass pollen allergy or for the preventive immunotherapy of grass pollen allergies.

16 Claims, 9 Drawing Sheets

Figure 1

| | | | | | | | | | | | | | | | | | | | | | | | | |
|---|---|---|---|---|---|---|---|---|---|---|---|---|---|---|---|---|---|---|---|---|---|---|---|---|
| 1 | – | I | P | K | V | P | P | G | P | N | I | T | A | T | Y | G | D | K | W | L | D | A | K | S | T | W | Y | G | K | – | P | Phl p 1 Wt GenBank Z27090 |
| 1 | – | I | A | K | V | P | P | G | P | N | I | T | A | T | Y | G | D | K | W | L | D | A | K | S | T | W | Y | G | K | – | P | Poa p 1 GenBank AJ131850 |
| 1 | – | I | A | K | V | P | P | G | P | N | I | T | A | T | Y | G | D | K | W | L | D | A | K | S | T | W | Y | G | K | – | P | Hol l 1 GenBank AJ012714 |
| 1 | – | I | A | K | V | P | P | G | P | N | I | T | A | E | Y | G | D | K | W | L | D | A | K | S | T | W | Y | G | K | – | P | Lol p 1 GenBank M35687 |
| 1 | A | M | G | D | – | K | P | G | P | N | I | T | A | T | Y | G | D | K | W | L | D | A | K | A | T | F | Y | G | S | D | P | Cyn d 1 GenBank AF177379 |
| 1 | G | P | P | K | V | P | P | G | P | N | I | T | I | S | Y | G | D | K | W | L | E | A | K | A | T | W | Y | G | A | – | P | Ory s 1 GenBank AF261270.1 |
| 1 | – | I | A | K | V | P | P | G | P | N | I | T | A | E | Y | G | D | K | W | L | D | A | K | S | T | W | Y | G | K | – | P | Pha a 1 GenBank S80654 |

| 30 | T | A | A | G | P | K | D | N | G | G | A | C | G | Y | K | D | V | D | K | P | P | F | S | G | M | T | G | C | G | N | T | Phl p 1 Wt GenBank Z27090 |
| 30 | T | G | A | G | P | K | D | N | G | G | A | C | G | Y | K | D | V | D | K | A | P | F | S | G | M | T | G | C | G | N | T | Poa p 1 GenBank AJ131850 |
| 30 | T | G | A | G | P | K | D | N | G | G | A | C | G | Y | K | D | V | D | K | P | P | F | S | G | M | T | G | C | G | N | T | Hol l 1 GenBank AJ012714 |
| 30 | T | G | A | G | P | K | D | N | G | G | A | C | G | Y | K | D | V | D | K | A | P | F | N | G | M | T | G | C | G | N | T | Lol p 1 GenBank M35687 |
| 31 | R | G | A | A | P | D | D | H | G | G | A | C | G | Y | K | D | V | D | K | A | P | F | D | G | M | T | G | C | G | N | E | Cyn d 1 GenBank AF177379 |
| 31 | K | G | A | G | P | K | D | N | G | G | A | C | G | Y | K | D | V | D | K | A | P | F | L | G | M | N | S | C | G | N | D | Ory s 1 GenBank AF261270.1 |
| 30 | T | G | A | G | P | K | D | N | G | G | A | C | G | Y | K | D | V | D | K | A | P | F | N | G | M | T | G | C | G | N | T | Pha a 1 GenBank S80654 |

| 61 | P | I | F | K | S | G | R | G | C | G | S | C | F | E | I | K | C | T | K | P | E | A | C | S | G | E | P | V | V | V | H | Phl p 1 Wt GenBank Z27090 |
| 61 | P | I | F | K | S | G | R | G | C | G | S | C | F | E | I | K | C | T | K | P | E | S | C | S | G | E | P | V | L | V | H | Poa p 1 GenBank AJ131850 |
| 61 | P | I | F | K | S | G | R | G | C | G | S | C | F | E | I | K | C | T | K | P | E | S | C | S | G | E | P | I | V | V | H | Hol l 1 GenBank AJ012714 |
| 61 | P | I | F | K | D | G | R | G | C | G | S | C | F | E | I | K | C | T | K | P | E | S | C | S | G | E | A | V | T | V | T | Lol p 1 GenBank M35687 |
| 62 | P | I | F | K | D | G | L | G | C | G | S | C | Y | E | I | K | C | K | E | P | A | E | C | S | G | E | P | V | L | I | K | Cyn d 1 GenBank AF177379 |
| 62 | P | I | F | K | D | G | K | G | C | G | S | C | F | E | I | K | C | S | K | P | E | A | C | S | D | K | P | A | L | I | H | Ory s 1 GenBank AF261270.1 |
| 61 | P | I | F | K | D | G | R | G | C | G | S | C | F | E | L | K | C | S | K | P | E | S | C | S | G | E | P | I | T | V | H | Pha a 1 GenBank S80654 |

| 92 | I | T | D | D | N | E | E | P | I | A | A | Y | H | F | D | L | S | G | I | A | F | G | S | M | A | K | K | G | D | E | Q | Phl p 1 Wt GenBank Z27090 |
| 92 | I | T | D | D | N | E | E | P | I | A | A | Y | H | F | D | L | S | G | K | A | F | G | A | M | A | K | K | G | E | E | Q | Poa p 1 GenBank AJ131850 |
| 92 | I | T | D | D | N | E | E | P | I | A | A | Y | H | L | D | L | S | G | K | A | F | G | A | M | A | K | K | G | E | E | Q | Hol l 1 GenBank AJ012714 |
| 92 | I | T | D | D | N | E | E | P | I | A | P | Y | H | F | D | L | S | G | H | A | F | G | S | M | A | K | K | G | E | E | Q | Lol p 1 GenBank M35687 |
| 93 | I | T | D | K | N | Y | E | H | I | A | A | Y | H | F | D | L | S | G | K | A | F | G | A | M | A | K | K | G | E | E | D | Cyn d 1 GenBank AF177379 |
| 93 | V | T | D | M | N | D | E | P | I | A | A | Y | H | F | D | L | S | G | L | A | F | G | A | M | A | K | K | D | G | K | D | E | Ory s 1 GenBank AF261270.1 |
| 92 | I | T | D | D | N | E | E | P | I | A | P | Y | H | F | D | L | S | G | H | A | F | G | S | M | A | K | K | G | E | E | E | Pha a 1 GenBank S80654 |

| 123 | K | L | R | S | A | G | E | V | E | I | Q | F | R | R | V | K | C | K | Y | P | E | G | T | K | V | T | F | H | V | E | K | Phl p 1 Wt GenBank Z27090 |
| 123 | K | L | R | S | A | G | E | L | E | L | K | F | R | R | V | K | C | E | Y | P | E | G | T | K | V | T | F | H | V | E | K | Poa p 1 GenBank AJ131850 |
| 123 | K | L | R | S | A | G | E | L | E | L | K | F | R | R | V | K | C | E | Y | P | K | G | T | K | V | T | F | H | V | E | K | Hol l 1 GenBank AJ012714 |
| 123 | N | V | R | S | A | G | E | L | E | L | Q | F | R | R | V | K | C | K | Y | P | D | D | T | K | P | T | F | H | V | E | K | Lol p 1 GenBank M35687 |
| 124 | K | L | R | K | A | G | E | L | M | L | Q | F | R | R | V | K | C | E | Y | P | S | D | T | K | I | T | F | H | V | E | K | Cyn d 1 GenBank AF177379 |
| 124 | E | L | R | K | A | G | I | I | D | I | Q | F | R | R | V | K | C | K | Y | P | A | D | T | K | I | T | F | H | I | E | K | Ory s 1 GenBank AF261270.1 |
| 123 | N | V | R | G | A | G | E | L | E | L | Q | F | R | R | V | K | C | K | Y | P | D | G | T | K | P | T | F | H | V | E | K | Pha a 1 GenBank S80654 |

| 154 | G | S | N | P | N | Y | L | A | L | L | V | K | F | V | A | G | D | G | D | V | V | A | V | D | I | K | E | K | G | K | D | Phl p 1 Wt GenBank Z27090 |
| 154 | G | S | N | P | N | Y | L | A | L | L | V | K | Y | V | T | G | D | G | D | V | V | A | V | D | I | K | E | K | G | K | D | Poa p 1 GenBank AJ131850 |
| 154 | G | S | N | P | N | Y | L | A | L | L | V | K | Y | V | D | G | D | G | D | V | V | A | V | D | I | K | E | K | G | K | D | Hol l 1 GenBank AJ012714 |
| 154 | G | S | N | P | N | Y | L | A | I | L | V | K | Y | V | D | G | D | G | D | V | V | A | V | D | I | K | E | K | G | K | D | Lol p 1 GenBank M35687 |
| 155 | G | S | S | P | N | Y | L | A | L | L | V | K | Y | A | A | G | D | G | N | I | V | G | V | D | I | K | P | K | G | S | D | Cyn d 1 GenBank AF177379 |
| 155 | A | S | N | P | N | Y | L | A | L | L | V | K | Y | V | A | G | D | G | D | V | V | E | V | E | I | K | E | K | G | S | E | Ory s 1 GenBank AF261270.1 |
| 154 | G | S | N | P | N | Y | L | A | L | L | V | K | Y | V | D | G | D | G | D | V | V | A | V | D | I | K | E | K | G | K | D | Pha a 1 GenBank S80654 |

| 185 | K | W | I | A | L | K | E | S | W | G | A | I | W | R | I | D | T | P | E | V | L | K | G | P | F | T | V | R | Y | T | T | Phl p 1 Wt GenBank Z27090 |
| 185 | K | W | I | E | L | K | E | S | W | G | S | I | W | R | V | D | T | P | D | K | L | I | G | P | F | T | V | R | Y | T | T | Poa p 1 GenBank AJ131850 |
| 185 | K | W | I | E | L | K | E | S | W | G | A | V | W | R | V | D | T | P | D | K | L | I | G | P | F | T | V | R | Y | T | T | Hol l 1 GenBank AJ012714 |
| 185 | K | W | I | E | L | K | E | S | W | G | A | V | W | R | I | D | T | P | D | K | L | I | G | P | F | T | V | R | Y | T | T | Lol p 1 GenBank M35687 |
| 186 | V | F | L | P | M | K | L | S | W | G | A | I | W | R | M | D | P | P | K | P | L | K | G | P | F | T | I | R | L | T | S | Cyn d 1 GenBank AF177379 |
| 186 | E | W | K | A | L | K | E | S | W | G | A | I | W | R | I | D | T | P | K | P | L | K | G | P | F | S | V | R | V | T | T | Ory s 1 GenBank AF261270.1 |
| 185 | K | W | I | E | L | K | E | S | W | G | A | I | W | R | I | D | T | P | D | K | L | I | G | P | F | T | V | R | Y | T | T | Pha a 1 GenBank S80654 |

| 216 | E | G | G | T | K | G | E | A | K | D | V | I | P | E | G | W | K | A | D | T | A | Y | E | S | – | – | – | – | K | Phl p 1 Wt GenBank Z27090 |
| 216 | E | G | G | T | K | G | E | A | E | D | V | I | P | E | G | W | K | A | D | T | A | Y | A | S | – | – | – | – | K | Poa p 1 GenBank AJ131850 |
| 216 | E | G | G | T | K | V | E | A | E | D | V | I | P | E | G | W | K | A | D | T | A | Y | E | S | – | – | – | – | K | Hol l 1 GenBank AJ012714 |
| 216 | E | G | G | T | K | S | E | V | E | D | V | I | P | E | G | W | K | A | D | T | S | Y | S | A | K | – | – | – | – | Lol p 1 GenBank M35687 |
| 217 | E | S | G | G | H | V | E | Q | E | D | V | I | P | E | D | W | K | P | D | T | V | Y | K | S | K | I | Q | E | | Cyn d 1 GenBank AF177379 |
| 217 | E | G | G | E | I | I | A | E | D | A | I | P | D | G | W | K | A | D | S | V | Y | K | S | N | V | Q | A | K | | | Ory s 1 GenBank AF261270.1 |
| 216 | E | G | G | T | K | A | E | E | E | D | V | I | P | E | G | W | K | A | D | T | – | H | D | A | S | – | – | – | K | Pha a 1 GenBank S80654 |

Figure 2

```
              10                  20                  30
1    I P K V P P G P N I T A T Y G D K W L D A K S T W Y G K P T   Phl p 1 Wt GenBank Z27090
1    I P K V P P G P N I T A T Y G D K W L D A K S T W Y G K P T   Phl p 1 NoCys 40                  50                  60
31   A A G P K D N G G A C G Y K D V D K P P F S G M T G C G N T   Phl p 1 Wt GenBank Z27090
31   A A G P K D N G G A [S] G Y K D V D K P P F S G M T G [S] G N T   Phl p 1 NoCys 70                  80                  90
61   P I F K S G R G C G S C F E I K C T K P E A C S G E P V V V   Phl p 1 Wt GenBank Z27090
61   P I F K S G R G [S] G S [S] F E I K [S] T K P E A [S] S G E P V V V   Phl p 1 NoCys

Figure 3

|     |     | 10  |     |     | 20  |     |     | 30  |     |
| --- | --- | --- | --- | --- | --- | --- | --- | --- | --- |
| 1   | I P K V P P | G P N I | T A T Y G D K W L | D A K S T | W Y G K P T | Phl p 1 NoCys |
| 1   | I P K V P P | G P N I | T A T Y G D K W L | D A K S T | W Y G K P T | Phl p 1 NoCys d213-220 |
| 1   | : : : : : : | G P N I | T A T Y G D K W L | D A K S T | W Y G K P T | Phl p 1 NoCys d1-6,115-119,213-220 |

|     | 40  |     | 50  |     | 60  |
| --- | --- | --- | --- | --- | --- |
| 31  | A A G P K D N G G A S | G Y K D V D K P P F | S G M T G S G N T | Phl p 1 NoCys |
| 31  | A A G P K D N G G A S | G Y K D V D K P P F | S G M T G S G N T | Phl p 1 NoCys d213-220 |
| 25  | A A G P K D N G G A S | G Y K D V D K P P F | S G M T G S G N T | Phl p 1 NoCys d1-6,115-119,213-220 |

|     | 70  |     | 80  |     | 90  |
| --- | --- | --- | --- | --- | --- |
| 61  | P I F K S G R G S G S | S F E I K S T K P E A | S S G E P V V V | Phl p 1 NoCys |
| 61  | P I F K S G R G S G S | S F E I K S T K P E A | S S G E P V V V | Phl p 1 NoCys d213-220 |
| 55  | P I F K S G R G S G S | S F E I K S T K P E A | S S G E P V V V | Phl p 1 NoCys d1-6,115-119,213-220 |

|     | 100 |     | 110 |     | 120 |
| --- | --- | --- | --- | --- | --- |
| 91  | H I T D D N E E P I | A A Y H F D L S G I | A F G S M A K K G D | Phl p 1 NoCys |
| 91  | H I T D D N E E P I | A A Y H F D L S G I | A F G S M A K K G D | Phl p 1 NoCys d213-220 |
| 85  | H I T D D N E E P I | A A Y H F D L S G I | A F G S : : : : : D | Phl p 1 NoCys d1-6,115-119,213-220 |

|     | 130 |     | 140 |     | 150 |
| --- | --- | --- | --- | --- | --- |
| 121 | E Q K L R S A G E V E I | Q F R R V K S K Y P E | G T K V T F H | Phl p 1 NoCys |
| 121 | E Q K L R S A G E V E I | Q F R R V K S K Y P E | G T K V T F H | Phl p 1 NoCys d213-220 |
| 110 | E Q K L R S A G E V E I | Q F R R V K S K Y P E | G T K V T F H | Phl p 1 NoCys d1-6,115-119,213-220 |

|     | 160 |     | 170 |     | 180 |
| --- | --- | --- | --- | --- | --- |
| 151 | V E K G S N P N Y L A L | L V K F V A G D G D V | V A V D I K E | Phl p 1 NoCys |
| 151 | V E K G S N P N Y L A L | L V K F V A G D G D V | V A V D I K E | Phl p 1 NoCys d213-220 |
| 140 | V E K G S N P N Y L A L | L V K F V A G D G D V | V A V D I K E | Phl p 1 NoCys d1-6,115-119,213-220 |

|     | 190 |     | 200 |     | 210 |
| --- | --- | --- | --- | --- | --- |
| 181 | K G K D K W I A L K E S | W G A I W R I D T P E | V L K G P F T | Phl p 1 NoCys |
| 181 | K G K D K W I A L K E S | W G A I W R I D T P E | V L K G P F T | Phl p 1 NoCys d213-220 |
| 170 | K G K D K W I A L K E S | W G A I W R I D T P E | V L K G P F T | Phl p 1 NoCys d1-6,115-119,213-220 |

|     | 220 |     | 230 |     | 240 |
| --- | --- | --- | --- | --- | --- |
| 211 | V R Y T T E G G T K | G E A K D V I | P E G W K A D T A Y E S K | Phl p 1 NoCys |
| 211 | V R : : : : : : : : | G E A K D V I | P E G W K A D T A Y E S K | Phl p 1 NoCys d213-220 |
| 200 | V R : : : : : : : : | G E A K D V I | P E G W K A D T A Y E S K | Phl p 1 NoCys d1-6,115-119,213-220 |

VARIANTS OF GROUP 1 ALLERGENS FROM *POACEAE* HAVING REDUCED ALLERGENICITY AND MAINTAINED T-CELL REACTIVITY

CROSS-REFERENCE TO RELATED APPLICATIONS

This application is the U.S. National Phase under §371 of International Application PCT/EP05/07481, filed Jul. 11, 2005, the disclosure in which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Sep. 1, 2011, is named MERCK3272.txt and is 72,031 bytes in size.

The present invention relates to the preparation and use of variants of the group 1 allergens of the Poaceae (sweet grasses) which are characterised by reduced IgE reactivity compared with the known wild-type allergens and at the same time by substantially maintained reactivity with T-lymphocytes. These hypoallergenic allergen variants can be employed for the specific immunotherapy (hyposensitisation) of patients having grass pollen allergy or for the preventive immunotherapy of grass pollen allergies A preferred embodiment of the invention relates to variants of the major allergen Phl p 1 from the pollen of timothy grass (*Phleum pratense*).

BACKGROUND OF THE INVENTION

Type 1 allergies have worldwide importance. Up to 20% of the population in industrialised countries suffer from complaints such as allergic rhinitis, conjunctivitis or bronchial asthma. These allergies are caused by allergens present in the air (aeroallergens) which are liberated by sources of various origin, such as plant pollen, mites, cats or dogs. Up to 40% of these type 1 allergy sufferers in turn exhibit specific IgE reactivity with grass pollen allergens (Freidhoff et al., 1986, J. Allergy Clin. Immunol. 78: 1190-2002). The substances which trigger type 1 allergy are proteins, glycoproteins or polypeptides. After uptake via the mucous membranes, these allergens react with the IgE molecules bound to the surface of mast cells in sensitised persons. Crosslinking of two IgE molecules with one another by an allergen results in the release of mediators (for example histamine, prostaglandins) and cytokines by the effector cell and thus in the corresponding clinical symptoms.

Depending on the relative frequency with which the individual allergen molecules react with the IgE antibodies of allergy sufferers, a distinction is made between major and minor allergens.

In the case of timothy grass (*Phleum pratense*), Phl p 1 (Petersen et al., 1993, J. Allergy Clin. Immunol. 92: 789-796), Phl p 5 (Matthiesen and Löwenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54). Phl p 2/3 (Dolecek et al., 1993, FEBS 335 (3), 299-304), Phl p 4 (Haavik et al., 1985, Int. Arch. Allergy Appl. Immunol. 78: 260-268; Valenta et al., 1992, Int. Arch. Allergy Immunol. 97: 287-294, Fischer et al., 1996, J. Allergy Clin. Immunol. 98: 189-198) and Phl p 13

(Suck et al., 2000, Clin. Exp. Allergy 30: 324-332; Suck et al., 2000, Clin. Exp. Allergy 30: 1395-1402) have hitherto been identified as major allergens.

The dominant major allergens of timothy grass (*Phleum pratense*) are Phl p 1 and Phl p 5. Since the major allergens of the grasses from the Poaceae family are highly homologous with one another and consequently have very similar biochemical and immunological properties, these related proteins are grouped together as group 1 and group 5 allergens.

The group 1 allergens react with the IgE antibodies in more than 95% of grass pollen allergy sufferers and are thus the dominant major allergens of grass pollen.

The group 1 allergens are glycoproteins having a molecular weight of about 32 kDa and are localised in the cytoplasm of the pollen grains. Both contact of the pollen grains with the mucous membrane of the upper respiratory tract and also moistening of the pollen grains by rain lead to rapid release of these allergens. The rapid release of the group 1 allergens, also in the form of sub-cellular microparticles, enables penetration into the lower respiratory tract, which can result in triggering of severe asthma attacks.

The cDNAs of group 1 allergens from *Phleum pretense* (Laffer et al., 1994, J. Allergy Clin. Immunol. 94: 689-698), *Lolium perenne* (Perez et al., 1990, J. Biol. Chem. 265: 16210-16250), *Holcus lanatus* (Schramm et al., 1997, J. Allergy Clin. Immunol. 1999:781-787), *Poa pratensis* (Sturaro u. Viotti, 1998, NCBI GenBank, Acc. No. AJ 131850), *Cynodon dactylon* (Smith et al., 1996, J. Allergy Clin. Immunol. 98: 331-343), *Phalaris aquatica* (Suphioglu et al., 1995, Clin. Exp. Allergy 25: 853-865) and *Oryza sativa* (Xu et al., 1995, Gene 164: 255-259) have been identified.

In addition to these first descriptions of the sequence, further group 1 allergen sequences which differ from the original sequences in individual positions have been published in databases. Such isoforms are also known for other grass pollen allergens.

Owing to their homology, the group 1 allergens of the sweet grasses (Poaceae) have high cross-reactivity with human IgE antibodies (Laffer et al., 1996, Mol. Immunology 33: 417-426). This immunological cross-reactivity is based on a very similar amino acid sequence, as shown by a sequence comparison of Phl p 1, the group 1 allergen of timothy grass (*Phleum pretense*), with group 1 molecules from selected species in FIG. 1.

Homologous sequence regions in the other group 1 allergens of the Poaceae exist both for the sequence regions of the Phl p 1 amino acid sequence deletions described here in the construction of hypoallergenic variants and also for the flanking sequence regions thereof. Furthermore, both the number and also the surrounding sequence regions of the cysteines of the group 1 allergens of the Poaceae are preserved. Owing to sequence homologies, the group 1 allergens of the Poaceae are classified in the protein family of the β-expansins (Cosgrove D. J., 2000 Nature 407: 321-6).

A classical approach to effective therapeutic treatment of allergies is specific immunotherapy or hyposensitisation (Fiebig, 1995, Allergo J. 4 (6): 336-339: Bousquet et al., 1998, J. Allergy Clin. Immunol. 102 (4): 558-562), where natural allergen extracts are injected subcutaneously into the patient in increasing doses. However, there is a risk in this method of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract. These T-cell epitopes are of crucial importance for the therapeutic action of the allergen preparations in hyposensitisation (Fiebig, 1995, Allergo J. 4 (7): 377-382).

A greater degree of therapy optimisation would be possible with allergens prepared by recombinant methods. Defined cocktails of high-purity allergens prepared by recombinant methods, if desired matched to the individual sensitisation patterns of patients, could supersede extracts from natural allergen sources since the latter, in addition to the various allergens, contain a relatively large number of immunogenic, but non-allergenic accompanying proteins.

Realistic perspectives which may result in safe hyposensitisation with recombinant expression products are offered by specifically mutated recombinant allergens in which IgE epitopes are specifically deleted without impairing the T-cell epitopes which are essential for the therapy (Schramm et al., 1999, J. Immunol. 162: 2406-2414).

A different concept for hyposensitisation is based on the fact that a protective immune response is induced, in particular, by IgG4 antibodies with a blocking action. In accordance with this hypothesis, recombinant Phl p 1 fragments have been described which are said to be suitable for induction of a protective IgG4 response (Ball et al., 1999, FASEB J. 13:1277-1290).

This concept is completely different from the concept of hypoallergenic allergen variants having reduced IgE reactivity and maintained T-cell reactivity.

Another possibility for influencing the disturbed T helper cell balance in allergy sufferers by therapeutic methods is treatment with expressible DNA which encodes for the relevant allergens (immunotherapeutic DNA vaccination). Experimental confirmation of the allergen-specific effect on the immune response has been obtained in rodents by injection of allergen-encoding DNA (Hsu et al., 1996, Nature Medicine 2 (5): 540-544).

The object on which the present invention is based consisted in the provision of novel variants of the group 1 allergens of the Poaceae at the protein and DNA level which are distinguished by reduced IgE activity with substantial maintenance of the T-cell reactivity and are therefore suitable for curative and preventive specific immunotherapy and immunotherapeutic DNA vaccination.

BRIEF DESCRIPTION OF THE DRAWINGS

FIG. 1: Alignment of Phl p 1-homologous amino acid sequences (sequences of mature proteins deduced from cDNA sequences) of Poaceae species: *Poa pratensis* (*Poa p*) (SEQ ID NO: 33), *Holcus lanatus* (*Hol l*) (SEQ ID NO: 34), *Lolium perenne* (*Lol p*) (SEQ ID NO: 35), *Cynodon dactylon* (*Cyn d*) (SEQ ID NO: 36), *Oryza sativa* (*Ory s*) (SEQ ID NO: 37) and *Phalaris aquatica* (*Pha a*) (SEQ ID NO: 38), protein sequences deduced from cDNA sequences from the "GenBank"database of the National Center for Biotechnology Information (NCBI, Bethesda, USA), numbering: amino acid positions of mature proteins, highlighted by underlining: amino acids which are different from the Phl p 1 sequence (SEQ ID NO: 32), black box: cysteines
FIG. 2: Alignment of amino acid sequences of processed Phl p1 wild-type protein (SEQ ID NO: 32) and the variant Phl p1 NoCys (SEQ ID NO: 39), Phl p1 Wt (wild type): protein sequence deduced from cDNA sequence ("GenBank" database entry Z27090 of the National Center for Biotechnology Information (NCBI), Bethesda, USA), numbering: amino acid positions of the mature protein, outlined in black: amino acid substitutions of cysteine by serine in protein Phl p 1 NoCys
FIG. 3: Alignment of amino acid sequences of the hypoallergenic variants Phl p 1 NoCys (SEQ ID NO: 39), Phl p 1 NoCys Δ213-220 (SEQ ID NO: 40) and Phl p 1 NoCys Δ1-6, 115-119, 213-220 (SEQ ID NO: 41), depicted by way of example, numbering: amino acid positions, highlighted by underlining: deletions

Figure 4:
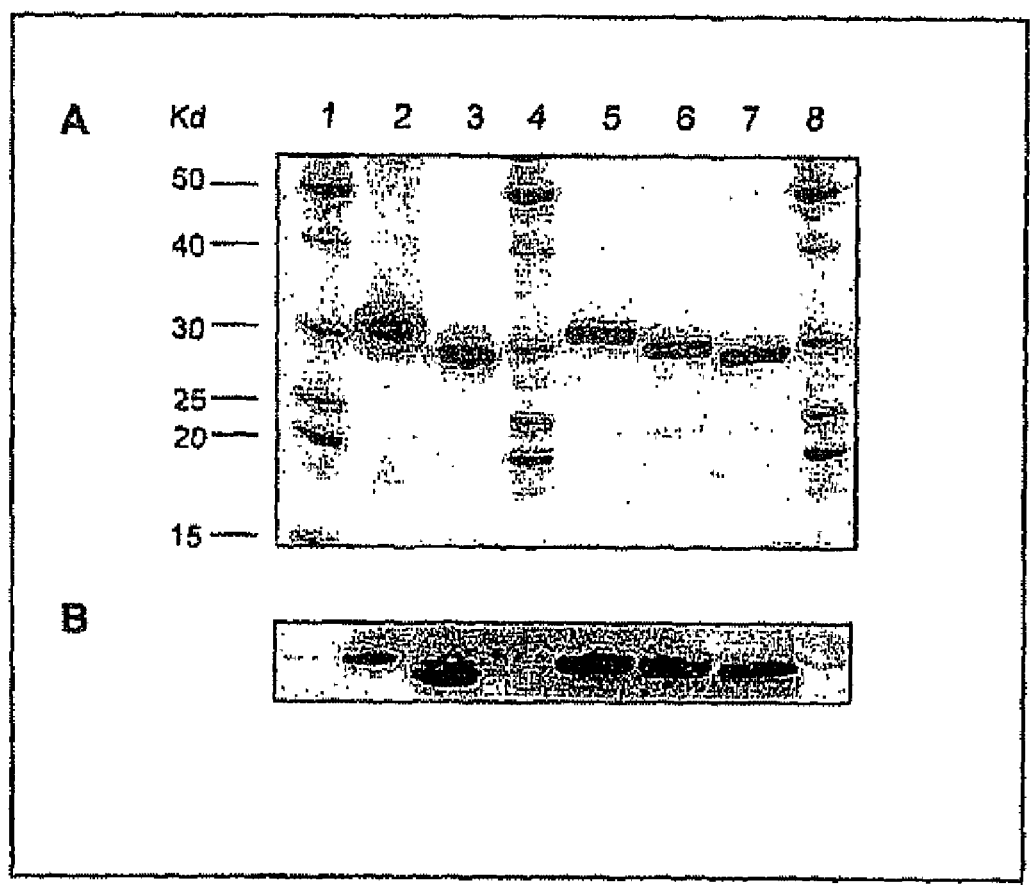
FIG. 4: SDS-PAGE and identity checking of the recombinant variants Phl p 1 NoCys, Phl p 1 NoCys Δ213-220 and Phl p 1 NoCys Δ1-6, 115-119, 213-220
A: SDS-PAGE
B: Western blot with aPhl p 1 antibodies (Allergopharma)
1. Marker proteins
2. nPhl p 1*
3. rPhl p 1 Wt (−His-tag)*
4. Marker proteins
5. Phl p 1 NoCys (+His-tag)
6. Phl p 1 NoCys D213-220 (+His-tag)
7. Phl p 1 NoCys D1-6, 115-119, 213-220 (+His-tag)
8. Marker proteins
* Samples reduced (dithiotreitol)

The work which led to the variants found was carried out using Phl p 1 as model allergen. It becomes clear from the sequence alignments shown in FIG. 1 that, owing to the high homology within group 1, the same results would have been obtained if the starting point had been another group 1 allergen.

Thus, it must also be assumed that the results given above and below can also be applied to Sec c 1 from *Secale cereale* or would have been obtained using Sec c 1, although the sequence is still unknown for this group 1 allergen.

The present invention therefore relates to variants of the group 1 allergens of the Poaceae which are characterised by reduced IgE reactivity compared with the known wild-type allergens and by maintained reactivity with T-lymphocytes. These group 1 allergens are preferably Phl p 1, Poa p 1, Hol p 1, Lol p 1, Cyn d 1, Ory s 1 and Pha a 1 from *Phleum pretense, Lolium perenne, Poa pratensis, Holcus lanatus, Cynodon dactylon, Oryza saliva* and *Phalaris aquatica*. Greater preference is given to Phl p 1, Poa p 1, Hol p 1, Lol p 1 or Pha a 1 and very particular preference is given to Phl p 1.

The starting point for the construction of the hypoallergenic variants of the group 1 allergens is the cDNA of wild-type Phl p 1, which was isolated with the aid of specific primers by polymerase chain reaction (PCR) from the total cDNA from pollen of *Phleum pretense* ("GenBank" entry Z27090; NCBI, Bethesda, USA) (SEQ ID NO 1).

The amino acid sequence SEQ ID NO 2 was deduced from the cDNA sequence of wild-type Phl p 1.

Phl p 1, which consists of 240 amino acids and is glycosylated in the natural form, is—like all group 1 allergens (see FIG. 1)—characterised by the existence of seven cysteines in the mature molecule. With the exception of Cyn d 1 and Ory s 1, these amino acid positions have the numbers 41, 57, 69, 72, 77, 83 and 139 in all group 1 allergens (Petersen et al., 1995, J. Allergy Clin. Immunol 95: 987-994).

Phl p 1 has been expressed in *E. coli* as non-glycosylated protein. The recombinant wild-type protein (rPhl p 1 wt) react with IgE antibodies from grass pollen allergy sufferers which have reactivity with natural purified Phl p 1 (nPhl p 1) (Petersen et al., 1998, Clin. Exp. Allergy 28: 315-321).

DETAILED DESCRIPTION OF THE INVENTION

Preparation and Characterisation of Hypoallergenic Phl p 1 Variants

Starting from the rPhl p 1 wt cDNA described, recombinant variants of Phl p 1 modified by genetic engineering were prepared.

The amino acid sequence of the recombinant variant Phl p 1 NoCys (SEQ ID NO 4) has seven serine residues instead of the seven cysteines occurring in the wild type (FIG. 2). The variant Phl p 1 NoCys served as starting point for the construction of various deletion mutants. In these, in each case individual sections having a length of 15 to 90 bp or combinations of these sections of the cDNA encoding for Phl p 1 NoCys have been deleted, resulting in corresponding deletions of amino acids 1-6, 1-30, 92-104, 115-119, 175-185 and 213-220 in the polypeptide chains of the proteins expressed in *E. coli*: Phl p 1 NoCys Δ1-6 (SEQ ID NO 5 and 6), Phl p 1 NoCys Δ1-30 (SEQ ID NO 7 and 8), Phl p 1 NoCys Δ92-104 (SEQ ID NO 9 and 10), Phl p 1 NoCys Δ115-119 (SEQ ID NO 11 and 12), Phl p 1 NoCys Δ175-185 (SEQ ID NO 13 and 14), Phl p 1 NoCys Δ213-220 (SEQ ID NO 15 and 16), as well as Phl p 1 NoCys Δ1-6, 115-119, 213-220 (SEQ ID NO 17 and 18).

The recombinant proteins were expressed as histidine fusion proteins in *Escherichia coli*. The immunological characterisation was carried out with fusion proteins of this type.

Firstly, after immobilisation on a nitrocellulose membrane, the recombinant variants were investigated for the ability to be bound by IgE antibodies of a representative serum pool and by IgE antibodies of individual sera from grass pollen allergy sufferers (strip test). In this method, reduced binding of IgE antibodies to Phl p 1 NoCys was surprisingly observed. This result was confirmed by an IgE inhibition test (EAST), in which the IgE binding capacity of an unimmobilised protein to IgE antibodies in solution is investigated.

The present invention therefore relates, in particular, to group 1 allergen variants in which the cysteines at amino acid positions 41, 57, 69, 72, 77, 83 and 139 corresponding to the mature Phl p 1 protein are removed or replaced by another amino acid. Particular preference is given here to corresponding variants of Phl p 1, Poa p 1, Hol p 1, Lol p 1 or Pha a 1, in particular of Phl p 1.

Reduced binding of IgE antibodies is already obtained if at least two of the 7 cysteines are removed without replacement or replaced by another amino acid, Preferably, however, all 7 cysteines are replaced by serine.

The effects of the reduced IgE binding capacity of Phl p 1 NoCys on the functional action during the crosslinking of membrane-bound IgE of the effector cells and activation thereof in vitro were investigated by means of an activation test of basophilic granulocytes from grass pollen allergy sufferers. Phl p 1 NoCys showed significantly lower activation of basophilic granulocytes here compared with rPhl p 1 wt and thus functionally reduced allergenicity.

The various deletion mutants prepared on the basis of Phl p 1 NoCys were investigated with respect to IgE binding capacity (strip test, EAST) and functional action (basophil activation) by the same method. Surprisingly, the deletion mutants exhibited particularly strong hypoallergenic properties.

The present invention therefore furthermore relates to group 1 allergen variants in which—optionally in addition to the above-described variants with removed or replaced Cys—at least one region or a combination of regions which correspond to amino acids 1-6, 1-30, 92-104, 115-119, 175-185 and 213-220 of the primary sequence of the mature Phl p 1 protein are missing compared with the wild-type allergen.

Particular preference is given here to the corresponding deletion mutants of the group 1 allergens Phl p 1, Poa p 1, Hol p 1, Lot p 1 and Pha a 1. Very particular preference is given to the corresponding Phl p 1 variants.

Particular preference is given, and the invention therefore likewise relates, to the group 1 allergen variants in which exclusively amino acids 213-220 or simultaneously amino acids 1-6 and 115-119 corresponding to the mature Phl p 1 sequence are missing. Greater preference is again given here to the allergens Phl p 1, Poa p 1, Hol p 1, Lol p 1 and Pha a 1, where Phl p 1 is very particularly preferred.

The T-cell reactivity of the hypoallergenic Phl p 1 variants which forms the basis for the efficacy of specific immunotherapy was checked in vitro by a proliferation test with Phl p 1-specific T-lymphocytes from grass pollen allergy sufferers. The modified allergens showed substantially maintained T-cell reactivity, which enables immunotherapeutic use of the hypoallergenic Phl p 1 variants.

The allergen variants according to the invention can be prepared starting from the cloned DNA sequence with the aid of genetic engineering methods. In principle, however, chemical modifications of the native allergen extract may also be involved (Fiebig, 1995, Allergo J. 4 (7), 377-382). Further modifications at different positions—for example in order to increase the hypoallergenicity—are of course also possible beyond the variations of group 1 allergens described in the present patent application. These modifications can be, for example, amino acid insertions, deletions and exchanges, cleavage of the protein into fragments and fusion of the protein or fragments thereof with other proteins or peptides. The invention furthermore relates to a DNA molecule, encoding for an allergen variant described above, a recombinant expression vector containing this DNA molecule and a host organism transformed with said DNA molecule or said expression vector. Suitable host organisms can be pro- or eukaryotic, single- or multicelled organisms, such as bacteria or yeasts. A host organism which is preferred in accordance with the invention is *E. coli*.

The invention furthermore relates to a process for the preparation of an allergen variant according to the invention by cultivation of the said host organism and isolation of the corresponding allergen variant from the culture.

The present invention additionally relates to the allergen variants, DNA molecules and expression vectors described above in their property as medicaments.

The present invention furthermore relates to pharmaceutical compositions comprising at least one of these allergen variants or a corresponding DNA molecule or a corresponding expression vector and optionally further active compounds and/or adjuvants for the treatment of allergies in the triggering of which group 1 allergens of the Poaceae are involved, or for the immunotherapeutic vaccination of patients having allergies in the triggering of which group 1 allergens of the Poaceae are involved, and/or for the prevention of such allergies.

If pharmaceutical compositions are of the second type (comprising at least one DNA molecule or an expression vector), these compositions preferably furthermore comprise aluminium hydroxide, an immunostimulatory CpG-containing oligonucleotide or a combination of the two as adjuvants.

For the purposes of this invention, pharmaceutical compositions can be used as therapeutic agents in human or veterinary medicine. Suitable excipients are organic or inorganic substances which are suitable for parenteral administration and do not react with group 1 allergen variants according to the invention. Suitable for parenteral use are, in particular, solutions, preferably oily or aqueous solutions, furthermore suspensions, emulsions or implants. The allergen variants according to the invention may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances and/or a plurality of further active compounds.

Furthermore, delayed-release preparations can be obtained by appropriate formulation of the allergen variants according to the invention, for example by adsorption onto aluminium hydroxide.

Finally, the present invention relates to the use of at least one allergen variant according to the invention or of a DNA molecule according to the invention or of an expression vector according to the invention for the preparation of a medicament for the treatment of allergies in the triggering of which group 1 allergens of the Poaceae are involved or for the immunotherapeutic vaccination of patients having allergies in the triggering of which group 1 allergens of the Poaceae are involved and/or for the prevention of such allergies.

The preparation of variants Phl p 1 NoCys, Phl p 1 NoCys Δ213-220 and Phl p 1 NoCys Δ1-6, 115-119, 213-220 (FIG. 3) and the immunological characterisation thereof is described below by way of example for the hypoallergenic Phl p 1 variants with the genetic engineering modifications described above.

Expression and Purification of Recombinant Phl p 1 Variants

The recombinant proteins were expressed as histidine fusion proteins (expression vector pProExHT; Invitrogen, Carlsbad, USA) in *Escherichia coli* (strain JM109). rPhl p 1 wt and the variants were firstly purified by specific binding of the N-terminal histidine residues to an $Ni^{2+}$ chelate matrix (immobilised metal ion affinity chromatography, IMAC) and subsequently by preparative gel filtration (size exclusion chromatography, SEC). The purity of the eluted proteins was monitored by SDS-PAGE and analytical SEC (FIG. 4a). The identity of the purified proteins was demonstrated by binding of a Phl p 1-specific monoclonal antibody (FIG. 4b).

Demonstration of Reduced IgE Binding of Recombinant Phl p 1 Variants

A simple test method for the determination of the IgE reactivity of specific IgE from sera from allergy sufferers on membrane-bound test proteins is the strip test.

For this purpose, the test substances are bound alongside one another in the same concentration and amount on a strip of nitrocellulose membrane under non-denaturing conditions. A series of such membrane strips can be incubated in parallel with different sera from allergy sufferers. After a washing step, the specifically bound IgE antibodies are rendered visible on the membrane by a colour reaction promoted by an anti-human IgE/alkaline phosphatase conjugate.

Figure 5:
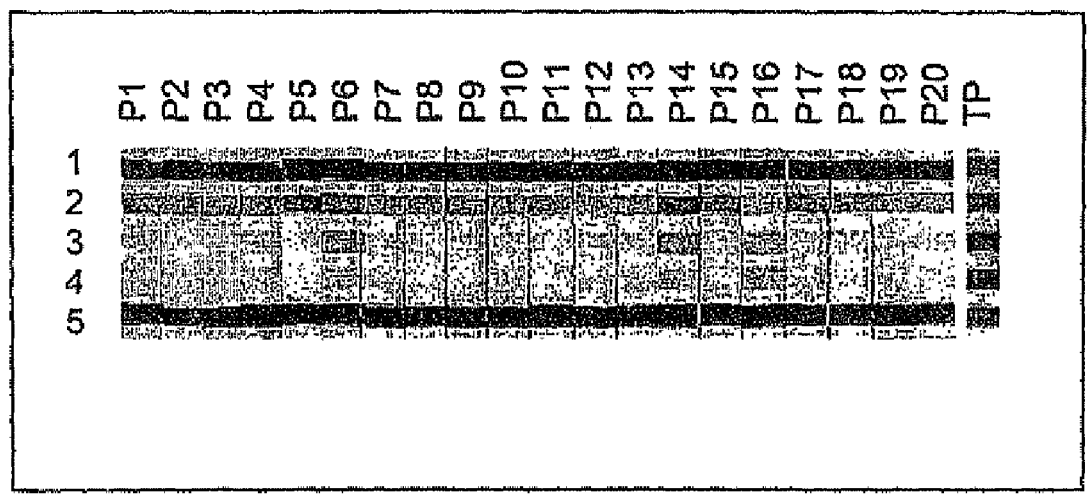
FIG. 5: Strip test for checking the IgE binding capacity of Phl p 1 NoCys, Phl p 1 NoCys Δ213-220 and Phl p 1 NoCys Δ1-6, 115-119, 213-220 under non-denaturing conditions
1) rPhl p 1 Wt
2) Phl p 1 NoCys
3) Phl p 1 NoCys D213-220
4) Phl p 1 NoCys D1-6, 115-119, 213-220
5) rPhl p 1 Wt
TP: total protein colouring
P: sera of clinically defined grass pollen allergy sufferers

The results of the strip test for Phl p 1 NoCys, Phl p 1 NoCys Δ213-220 and Phl p 1 NoCys Δ1-6, 115-119, 213-220 using sera from individual grass pollen allergy sufferers are depicted here by way of example for the modified Phl p 1 molecules described (FIG. 5).

Only sera from allergy sufferers having a strong IgE titre against natural Phl p 1 were used. The IgE antibodies from these patients likewise react with the recombinant equivalent rPhl p 1 wt.

It becomes clear that the Phl p 1-specific IgE antibodies of all patient sera bind the recombinant variant Phl p 1 NoCys to a reduced extent, but not the wild-type allergen Phl p 1.

An even greater reduction in the IgE binding capacity is achieved by the additional removal of certain sequence sections, which is depicted with reference to the variant Phl p 1 NoCys Δ213-220. The variant Phl p 1 NoCys Δ213-220 shows a very greatly reduced IgE binding capacity with all tested sera from allergy sufferers compared with the unmodified recombinant wild-type protein. A further reduction in the IgE binding capacity of Phl p 1 to IgE antibodies from certain sera can be achieved by combination of a number of deletions, which is evident from the test result for the variant Phl p 1 NoCys Δ1-6, 115-119, 213-220 with grass pollen allergy sufferer serum P14 (FIG. 5).

It thus becomes clear that both substitution of cysteines and also deletion of specific sequence sections reduces the IgE binding capacity of the Phl p 1 molecule.

In contrast to the strip test, the EAST inhibition test (enzyme allergosorbent test) enables the investigation of allergen/IgE interactions in solution, enabling interfering masking of epitopes of the test substance to be basically excluded by immobilisation onto the membrane.

The EAST inhibition test is carried out as follows. Microtitre plates are coated with allergens, here nPhl p 1. After removal of the unbound allergen molecules by washing, the plate is blocked using bovine serum albumin in order to prevent later nonspecific binding. IgE antibodies from allergy sufferers, as a representative pool of individual sera (serum pool) or as individual serum, is incubated in suitable dilution with the allergen-coated microtitre plates. The amount of allergen-bound IgE antibodies is quantified photometrically via an anti-hIgE/alkaline phosphatase conjugate by reaction of a substrate to give a coloured end product.

The binding of the IgE antibodies is inhibited substance-specifically by a soluble allergen or the substance to be tested (recombinant modified allergen) as a function of the concentration.

The test results for Phl p 1 NoCys, Phl p 1 NoCys Δ213-220 and Phl p 1 NoCys Δ1-6, 115-119, 213-220 are shown here by way of example for the modified Phl p 1 molecules described compared with the reference molecule nPhl p 1.

Figure 6:
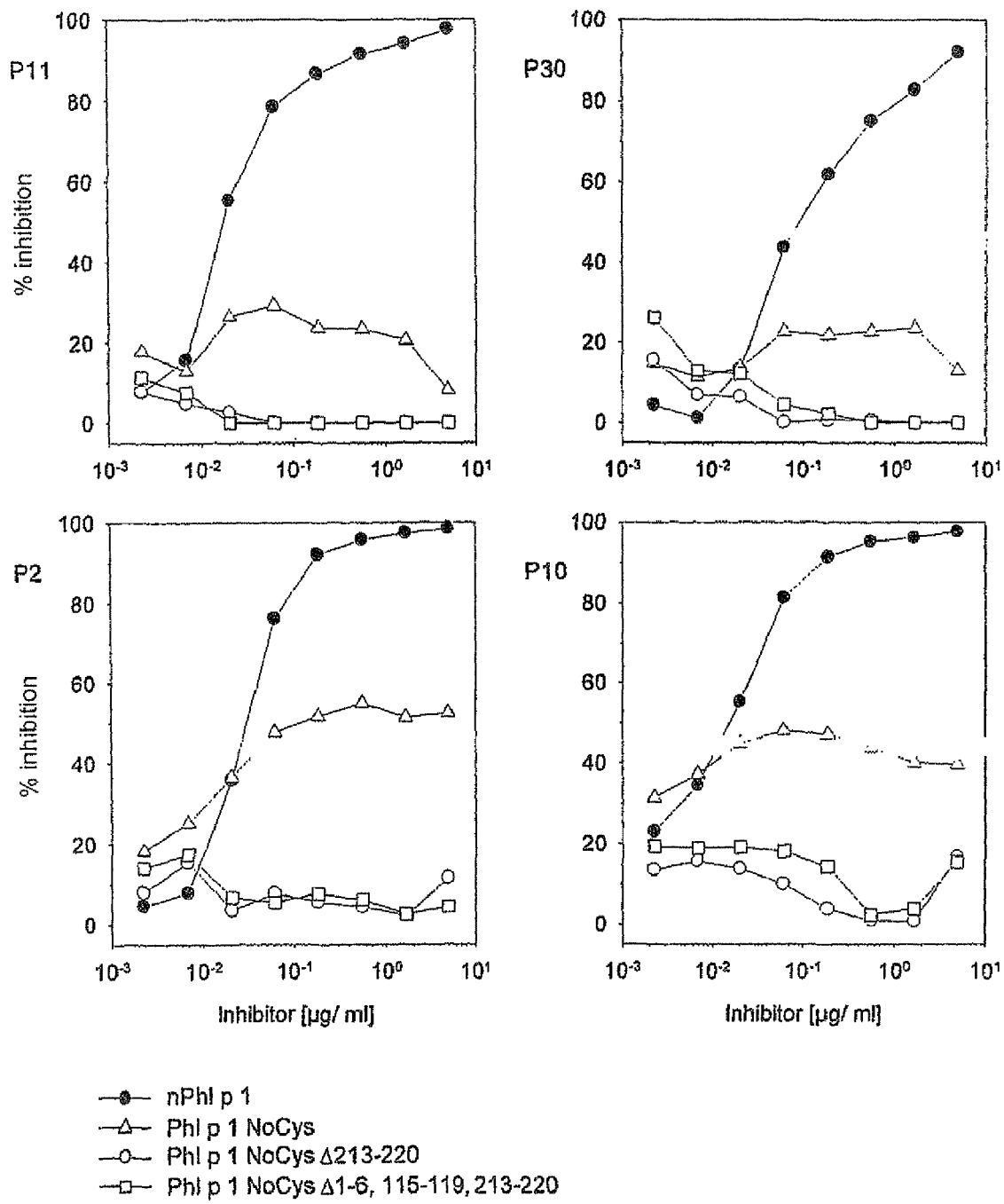
FIG. 6: Determination of the reduced IgE reactivity of Phl p 1 NoCys, Phl p 1 NoCys Δ213-220 and Phl p 1 NoCys Δ1-6, 115-119, 213-220 by means of the EAST inhibition test with four representative sera from grass pollen allergy sufferers (P)

The representative IgE inhibition tests shown in FIG. 6, with four individual sera from grass pollen allergy sufferers, show that only about 20-50% of the maximum inhibitory action of the unmodified natural allergen nPhl p1 was achieved, even with high concentrations of the variant Phl p 1 NoCys (up to 5 µg/ml). The lower maximum inhibitory action indicates a loss of IgE epitopes.

The curves for the variants Phl p 1 NoCys Δ213-220 and Phl p 1 NoCys Δ1-6, 115-119, 213-220 demonstrate an even lower IgE binding capacity of these Phl p 1 variants. An inhibitory action could not be detected with individual variation or only to a very small extent (0-20% of the maximum inhibitory action).

In agreement with the result of the strip test, it can thus be confirmed that the insertion of additional specific deletions further reduces the IgE binding capacity of Phl p 1.

Determination of the Hypoallergenicity of Recombinant Phl p 1 Variants by the Basophil Activation Test The functional reduction in allergenicity was determined in vitro by means of a basophil activation test. For the basophil activation test, heparinised whole blood from grass pollen allergy sufferers is incubated with various concentrations of the test substances. The allergenic substances are specifically bound by the FcεRI-bound IgE antibodies of the basophils and result in crosslinking of the FcεRI molecules.

This allergen-induced, IgE-promoted FcεRI crosslinking results in activation of the basophils. The activation is the first step in the allergic reaction of these effector cells. The subsequent signal transduction results in degranulation of the effector cells and thus in triggering of the allergic reactions in vivo.

In vitro, the allergen-induced activation of basophilic granulocytes can be determined by quantification of the expression of a surface protein (CD203c) which is coupled to signal transduction of the IgE receptor cross-linking (Kahlert et al., 2003, Cli., Exp. Allergy 33: 1266-72). The number of expressed CD203c proteins on a cell and the percentage of activated cells of a cell pool is measured with high sensitivity via the binding of a fluorescence-labelled monoclonal antibody to the surface marker and subsequent analysis by fluorescence-activated flow cytometry. The reference sub-stances employed here was purified natural Phl p 1 (nPhl p 1) in parallel with the test substances. The results for Phl p 1 NoCys, Phl p 1 NoCys Δ213-220 and Phl p 1 NoCys Δ1-6, 115-119, 213-220 are shown here by way of example for the modified Phl p 1 molecules described.

Figure 7:
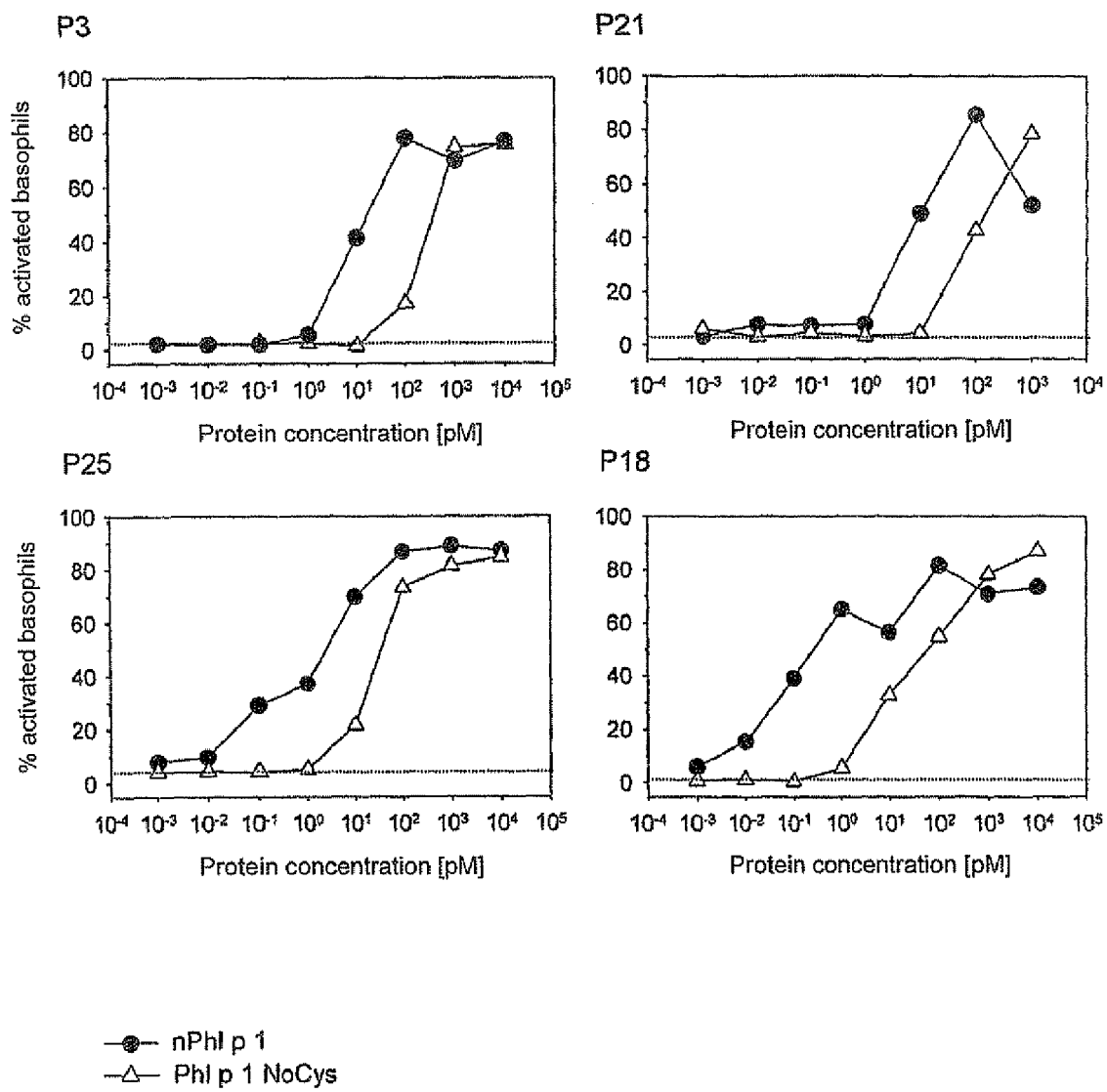
FIG. 7: Determination of the hypoallergenicity of Phl p 1 NoCys by means of the basophil activation test with basophils from four grass pollen allergy sufferers (P)

Representative test results for the variant Phl p 1 NoCys with basophils from four clinically defined allergy sufferers are shown as curves in FIG. 7. The reduction in the allergenic efficacy of the variant Phl p 1 NoCys relative to wild-type nPhl p 1 becomes clear through the shift in the activation curves.

Figure 8:
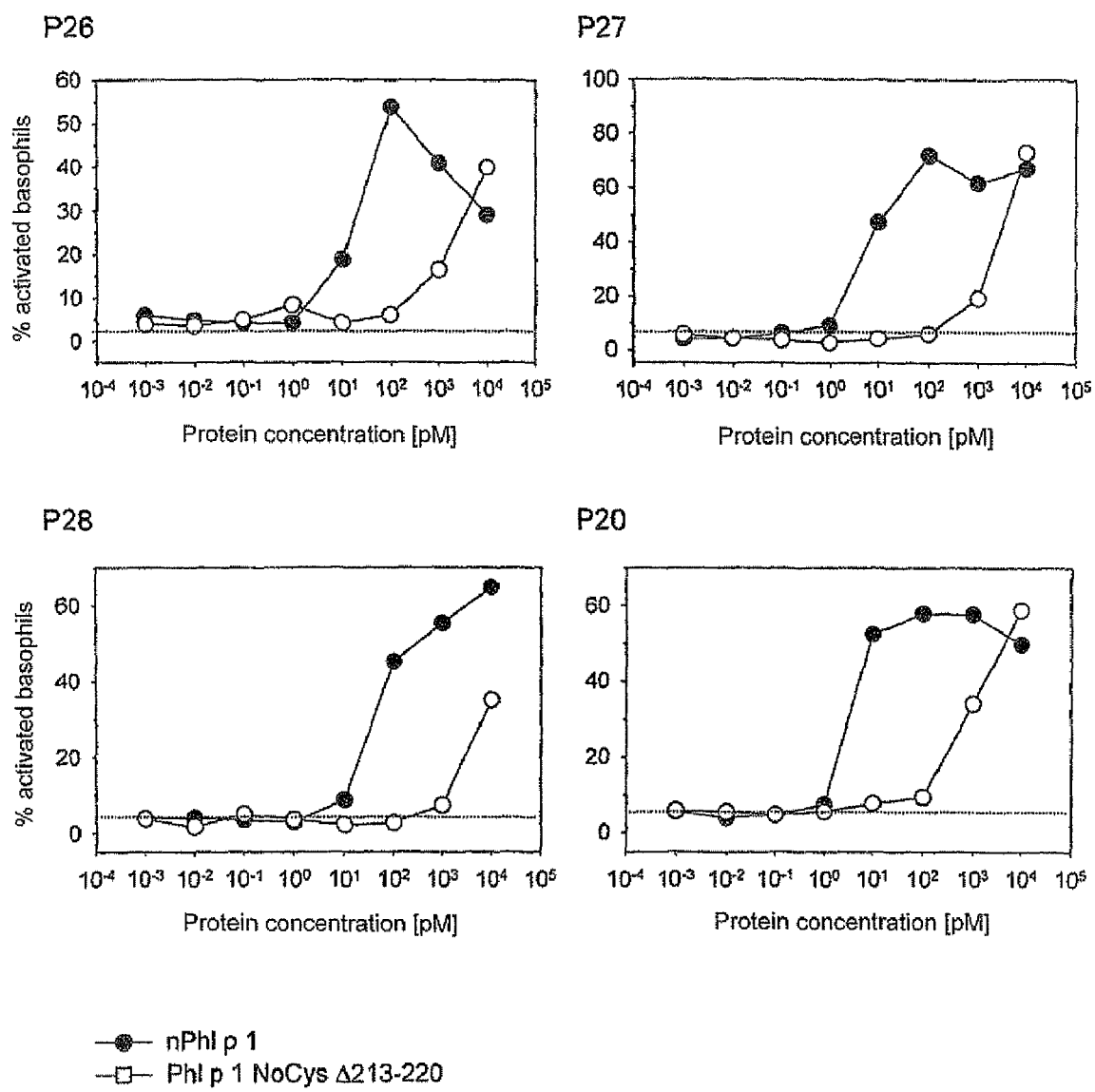
FIG. 8: Determination of the hypoallergenicity of Phl p 1 NoCys Δ213-220 by means of the basophil activation test with basophils from four grass pollen allergy sufferers (P)
Figure 9:
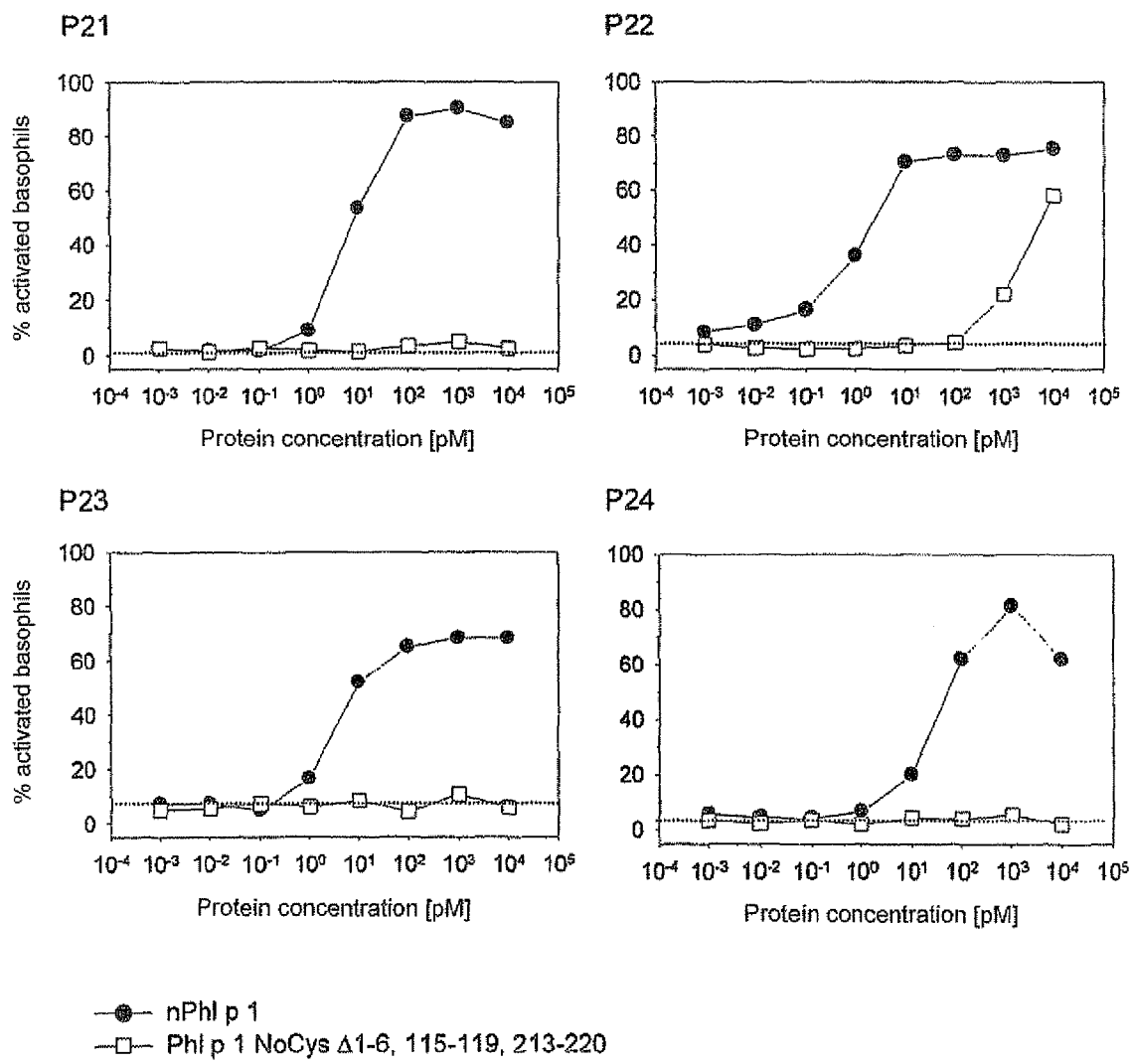
FIG. 9: Determination of the hypoallergenicity of Phl p 1 NoCys Δ1-6, 115-119, 213-220 by means of the basophil activation test with basophils from four grass pollen allergy sufferers (P)

In accordance with the results from the strip test and the IgE inhibition test, the test results for the variants Phl p 1 NoCys Δ213-220 and Phl p 1 NoCys Δ1-6, 115-119, 213-220 indicate an even greater reduction in the relative allergenic efficacy, as shown in FIGS. 8 and 9 with reference to representative curves.

Whereas a maximum proportion of basophils has already been activated by the natural allergen in a concentration range of the test substances of 100-1000 pM, no or only very little basophil activation was detected on use of the modified allergens Phl p 1 NoCys Δ213-220 and Phl p 1 NoCys Δ1-6, 115-119, 213-220.

The allergenic efficacy of variant Phl p 1 NoCys Δ213-220 was, as can be calculated by the A50 values of the curves, reduced ~100-1000 fold and that of variant Phl p 1 NoCys Δ1-6, 115-119, 213-220 was reduced more than 1000 fold compared with the reference nPhl p 1 (A50: allergen concentration at 50% of the maximum number of activated basophils).

T-Cell Reactivity of the Hypoallergenic Phl p 1 Variants

T helper lymphocytes react with allergen peptide fragments (about 12-25 amino acids) which are formed by enzymatic degradation in antigen-presenting cells (APCs) and are presented to the T-cells after inclusion of the suitable peptides into the individual MHC class II molecules at the surface of the APCs. This allergen-specific activation of the T helper lymphocytes is the prerequisite for proliferation and functional differentiation (TH1 and TH2). Influencing of the allergen-specific T-lymphocytes by treatment with allergen or an allergen derivative during hyposensitisation is regarded as the key for the therapeutic efficacy.

In order to investigate the T-cell reactivity, oligoclonal T-cell lines from grass pollen allergy sufferers are established by conventional methods with stimulation by nPhl p 1 or rPhl p 1 wt molecules. In a proliferation test, the various T-cell lines were stimulated with the reference allergens nPhl p 1 and rPhl p 1 wt and the modified recombinant Phl p 1 variants. The proliferation rate was determined by the incorporation of [$^3$H]-thymidine by conventional methods.

The results of the proliferation test of Phl p 1 NoCys, Phl p 1 NoCys Δ213-220 and Phl p 1 NoCys Δ1-6, 115-119, 213-220 are shown here by way of example for the modified Phl p 1 molecules described.

The results with T-cell lines from eight grass pollen allergy sufferers depicted in Table 1 show that it was possible to stimulate the T-lymphocytes to proliferation by the recombinant allergen variants. The T-cell reactivity of Phl p 1 NoCys, Phl p 1 NoCys Δ213-220 and Phl p 1 NoCys Δ1-6, 115-119, 213-220 is only reduced slightly compared with the unmodified natural and recombinant wild-type allergens, which demonstrates the retention of the crucial T-cell epitopes

TABLE 1

Determination of the T-cell reactivity of Phl p 1 NoCys, Phl p 1 NoCys Δ213-220 and Phl p 1 NoCys Δ1-6, 115-119, 213-220 by means of proliferation tests with Phl p 1-reactive T-cell lines (TCLs)

| | | Stimulation index[1] | | | | |
|---|---|---|---|---|---|---|
| Donor[2] | TCL | nPhl p 1 | rPhl p 1 Wt | Phl p 1 NoCys | Phl p 1 NoCys Δ213-220 | Phl p 1 NoCys Δ1-6, 115-119, 213-220 |
| A | 11.16 | 3.2 | 4.7 | 3.7 | 3.5 | 3.9 |
| B | 21.1 | 23.5 | 13.9 | 12.1 | 13.0 | 12.3 |
| C | 60.51 | 3.9 | 5.7 | 3.9 | 4.2 | 2.0 |
| D | 104.8 | 2.6 | 4.6 | 4.1 | 3.4 | 3.0 |
| E | 10.27 | 26.4 | 27.8 | 32.7 | 30.8 | 31.4 |
| F | 41.8 | 2.7 | 4.9 | 3.5 | 3.0 | 3.1 |
| G | 55.74 | 7.6 | 8.4 | 4.9 | 4.6 | 4.5 |
| H | 57.43 | 3.1 | 4.0 | 3.0 | 2.6 | 2.9 |

[1]Calculated from [$^3$H] measurement values, cpm measurement values of allergen-stimulated cell cultures/cpm measurement values of unstimulated cell cultures
[2]Donor: clinically defined grass pollen allergy sufferers Construction of Hypoallergenic Phl p 1 Variants by Genetic Engineering

EXAMPLE 1

Phl p 1 NoCys

For the construction of variant Phl p 1 NoCys (SEQ ID NO 3 and 4), six PCR steps were carried out starting from the cDNA of rPhl p 1 wt ("GenBank" entry Z27090; NCBI, Bethesda, USA). The point mutations were introduced using specific PCR primers which contained codons encoding for serine instead of those for cysteine (primer sequences see Table 2).

Step 1—Preparation of N-terminal DNA fragment "Phl p 1 [C41S, C57S, C69S] (bp 1-212)": a DNA fragment containing mutations C41S, C57S, C69S was generated by amplification of long overlapping oligonucleotides (P 1-63, P 49-111, P 97-158 and P 144-212) by means of PCR.

Step 2—Preparation of C-terminal DNA fragment "Phl p 1 [C69S, C72S, C77S, C83S] (bp 193-720)": PCR of Phl p 1 wt-cDNA with primers P 193-261 and P 703-720 HindIII.

Step 3—Preparation of the DNA encoding for "Phl p 1 [C41S, C57S, C69S, C72S, C77S, C83S] (bp 1-720)": PCR of overlapping fragments "Phl p 1 [C41S, C57S, C69S] (bp 1-212)" and "Phl p 1 [C69S, C72S, C77S, C83S] (bp 193-720)" with primers P 1-63 and P 703-720 HindIII.

Step 4—Preparation of N-terminal DNA fragment "Phl p 1 [C41S, C57S, C69S, C72S, C77S, C83S, C139S] (bp 1-428)": PCR of the cDNA of "Phl p 1 [C41S, C57S, C69S, C72S, C77S, C83S] (bp 1-720)" with primers P 1-63 and P 406-428 as.

Step 5—Preparation of C-terminal DNA fragment "Phl p 1 [C139S] (bp 406-720)":
PCR of the cDNA of rPhl p 1 wt with primers P 406-428s and P 703-720 HindIII.

Step 6—Preparation of the complete DNA encoding for Phl p 1 NoCys: PCR of overlapping fragments "Phl p 1 [C41S, C57S, C69S, C72S, C77S, C83S, C139S] (bp 1-428)" and "Phl p 1 [C139S] (bp 406-720) with primers P 1-63 and P 703-720 HindIII".

The DNA encoding for Phl p 1 NoCys were digested using the restriction enzyme HindIII and ligated into the expression vector pProExHT (Invitrogen, Carlsbad, USA) via restriction sites EheI and HindIII and subsequently sequenced in full.

TABLE 2

PCR primers employed for the preparation of Phl p 1 NoCys, Phl p 1 NoCys Δ213-220 and Phl p 1 NoCys Δ1-6, 115-119, 213-220

| Primer | Direction | SEQ ID NO | Sequence (5'→3') |
|---|---|---|---|
| P 1-18[1] | sense | 19 | atc ccg aag gtc ccg ccg |
| P 1-63 | sense | 20 | atc ccg aag gtc ccg ccg aac atc acg gcg acc tac ggc gac aag tgg ctg gac gcg |
| P 49-111 | antisense | 21 | gtt gtc ctt ggg acc ggc ggc cgt cgg ctt gcc gta cca ggt gct ctt cgc gtc cag cca ctt |
| P 97-158 | sense | 22 | ggt ccc aag gac aac ggc ggc gcg agc ggg tac aag gac gtg gac aag ccc ccg ttc agc gg |
| P 144-212 | antisense | 23 | gag ccg ct gcc ccg gcc gga ctt gaa gat ggg ggt gtt gcc gga gcc ggt cat gcc gct gaa cgg ggg c |
| P 193-261 | sense | 24 | tcc ggc cgg ggc agc ggc tcc tcc ttc gag atc aag agc acc aag ccc gag gcc tcc tcc ggc gag ccc |
| P 703-720 HindIII | antisense | 25 | ggt aag ctt tca ctt gga ctc gta ggc ggt |
| P 406-428 as | antisense | 26 | tcc ggg tac ttg gac ttg acg cg |
| P 406-428 s | sense | 27 | cgc gtc aag tcc aag tac ccg ga |
| P 22-63 (Δ1-18) | sense | 28 | ccg aac atc acg gcg acc tac ggc gac aag tgg ctg gac gcg |
| P 250-318 | antisense | 29 | gtc gaa gtg gta cgc ggc gat ggg ctc ctc gtt gtc gtc ggt gat gtg gac cac cac ggg ctc gcc gga |
| P 301-384 (Δ343-357) | sense | 30 | gcc gcg tac cac ttc gac ctc tcc ggc atc gcg ttc ggg tcc gac gag cag aag ctg cgc agc gcc ggc |
| P 613-720 (Δ637-660) | antisense | 31 | ggt aag ctt tca ctt gga ctc gta ggc ggt gtc ggc ctt cca gcc ctc ggg gat |

TABLE 2-continued

PCR primers employed for the preparation of Phl p 1 NoCys, Phl p 1 NoCys Δ213-220 and Phl p 1 NoCys Δ1-6, 115-119, 213-220

| Primer | Direction | SEQ ID NO | Sequence (5'→3') |
|---|---|---|---|
| HindIII | | | gac gtc ctt ggc ctc gcc gcg gac ggt gaa ggg gcc ctt gag |

[1]Numbers indicated: positions of the primers based on the nucleotide sequence of Phl p 1 wild-type protein (without signal peptide; "GenBank" entry Z27090; NCBI, Bethesda, USA). Primer sequences in some cases codon-optimised for *E. coli*.

EXAMPLE 2

Phl p 1 NoCys Δ213-220

The DNA sequence encoding for deletion variant Phl p 1 NoCys Δ213-220 (SEQ ID NO 15 and 16) was generated by means of PCR of the DNA of Phl p 1 NoCys using the 5'-primer P 1-18 and the 3'-primer P 613-720 (Δ637-660) HindIII specifically shortened by the sequence region to be deleted.

The cDNA were digested using the restriction enzyme HindIII and ligated into the expression vector pProExHT (Invitrogen, Carlsbad, USA) via restriction sites EheI and HindIII and subsequently sequenced in full.

EXAMPLE 3

Construction of Phl p 1 NoCys Δ1-6, 115-119, 213-220 by Genetic Engineering

The DNA sequence encoding for deletion variant Phl p 1 NoCys Δ1-6, 115-119, 213-220 (SEQ ID NO 5 and 6) was generated in three steps by means of PCR using oligonucleotides specifically shortened by the sequence region to be deleted.

Step 1—Preparation of N-terminal DNA fragment "Phl p 1 NoCys Δ1-6 (bp 1-300)": PCR of the cDNA of Phl p 1 NoCys with primers P22-63 (Δ1-18) and P 250-318.

Step 2—Preparation of C-terminal DNA fragment "Phl p 1 NoCys Δ115-119, 213-220 (bp 283-663)": PCR of Phl p 1 NoCys with primers P 301-384 (Δ343-357) and P 613-720 (Δ637-660) HindIII.

Step 3—Preparation of the complete DNA encoding for Phl p 1 NoCys Δ1-6, 115-119, 213-220:
PCR of overlapping fragments "Phl p 1 NoCys Δ1-6 (bp 1-300)" and "Phl p 1 NoCys Δ115-119, 213-220 (bp 283-663)" with primers P22-63 (Δ1-18) and P 703-720 HindIII.

The DNA encoding for Phl p 1 NoCys Δ1-6, 115-119, 213-220 was digested using the restriction enzyme HindIII and ligated into the expression vector pProExHT (invitrogen, Carlsbad, USA) via restriction sites EheI and HindIII and subsequently sequenced in full.

The DNA of variants Phl p 1 NoCys Δ1-6 (SEQ ID NO 5 and 6), Phl p 1 NoCys Δ1-30 (SEQ ID NO 7 and 8), Phl p 1 NoCys Δ92-104 (SEQ ID NO 9 and 10), Phl p 1 NoCys Δ115-119 (SEQ ID NO 11 and 12), Phl p 1 NoCys Δ175-185 (SEQ ID NO 13 and 14) were prepared, cloned and sequenced correspondingly.

SEQUENCE LISTING

<160> NUMBER OF SEQ ID NOS: 41

<210> SEQ ID NO 1
<211> LENGTH: 723

-continued

```
<212> TYPE: DNA
<213> ORGANISM: Phleum pratense
<220> FEATURE:
<221> NAME/KEY: CDS
<222> LOCATION: (1)..(720)

<400> SEQUENCE: 1 atc ccc aag gtc ccc ccc ggc ccg aac atc acg gcg acc tac ggc gac      48
Ile Pro Lys Val Pro Pro Gly Pro Asn Ile Thr Ala Thr Tyr Gly Asp
 1               5                  10                  15 aag tgg ctg gac gcg aag agc acc tgg tac ggc aag ccg acg gcc gcc      96
Lys Trp Leu Asp Ala Lys Ser Thr Trp Tyr Gly Lys Pro Thr Ala Ala
             20                  25                  30 ggt ccc aag gac aac ggc ggc gcg tgc ggg tac aag gac gtg gac aag     144
Gly Pro Lys Asp Asn Gly Gly Ala Cys Gly Tyr Lys Asp Val Asp Lys
         35                  40                  45 ccc ccg ttc agc ggc atg acc ggc tgc ggc aac acc ccc atc ttc aag     192
Pro Pro Phe Ser Gly Met Thr Gly Cys Gly Asn Thr Pro Ile Phe Lys
     50                  55                  60 tcc ggc cgg ggc tgc ggc tcc tgc ttc gag atc aag tgc acc aag ccc     240
Ser Gly Arg Gly Cys Gly Ser Cys Phe Glu Ile Lys Cys Thr Lys Pro
 65                  70                  75                  80 gag gcc tgc tcc ggc gag ccc gtg gtg gtc cac atc acc gac gac aac     288
Glu Ala Cys Ser Gly Glu Pro Val Val Val His Ile Thr Asp Asp Asn
                 85                  90                  95 gag gag ccc atc gcc gcg tac cac ttc gac ctc tcc ggc atc gcg ttc     336
Glu Glu Pro Ile Ala Ala Tyr His Phe Asp Leu Ser Gly Ile Ala Phe
            100                 105                 110 ggg tcc atg gcc aag aag ggc gac gag cag aag ctg cgc agc gcc ggc     384
Gly Ser Met Ala Lys Lys Gly Asp Glu Gln Lys Leu Arg Ser Ala Gly
        115                 120                 125 gag gtg gag atc cag ttc cgc cgc gtc aag tgc aag tac ccg gag ggc     432
Glu Val Glu Ile Gln Phe Arg Arg Val Lys Cys Lys Tyr Pro Glu Gly
    130                 135                 140 acc aag gtc acc ttc cac gtg gag aag ggg tcc aac ccc aac tac ctg     480
Thr Lys Val Thr Phe His Val Glu Lys Gly Ser Asn Pro Asn Tyr Leu
145                 150                 155                 160 gcg ctg ctg gtg aag ttt gtc gcc ggc gac ggc gac gtg gtg gcg gtg     528
Ala Leu Leu Val Lys Phe Val Ala Gly Asp Gly Asp Val Val Ala Val
                165                 170                 175 gac atc aag gag aag ggc aag gac aag tgg atc gcg ctc aag gag tcg     576
Asp Ile Lys Glu Lys Gly Lys Asp Lys Trp Ile Ala Leu Lys Glu Ser
            180                 185                 190 tgg gga gcc atc tgg agg atc gac acc ccg gag gtg ctc aag ggc ccc     624
Trp Gly Ala Ile Trp Arg Ile Asp Thr Pro Glu Val Leu Lys Gly Pro
        195                 200                 205 ttc acc gtc cgc tac acc acc gag ggc ggc acc aag ggc gag gcc aag     672
Phe Thr Val Arg Tyr Thr Thr Glu Gly Gly Thr Lys Gly Glu Ala Lys
    210                 215                 220 gac gtc atc ccc gag ggc tgg aag gcc gac acc gcc tac gag tcc aag     720
Asp Val Ile Pro Glu Gly Trp Lys Ala Asp Thr Ala Tyr Glu Ser Lys
225                 230                 235                 240 tga                                                                 723

<210> SEQ ID NO 2
<211> LENGTH: 240
<212> TYPE: PRT
<213> ORGANISM: Phleum pratense

<400> SEQUENCE: 2

Ile Pro Lys Val Pro Pro Gly Pro Asn Ile Thr Ala Thr Tyr Gly Asp
 1               5                  10                  15
```

```
Lys Trp Leu Asp Ala Lys Ser Thr Trp Tyr Gly Lys Pro Thr Ala Ala
             20                  25                  30

Gly Pro Lys Asp Asn Gly Gly Ala Cys Gly Tyr Lys Asp Val Asp Lys
         35                  40                  45

Pro Pro Phe Ser Gly Met Thr Gly Cys Gly Asn Thr Pro Ile Phe Lys
 50                  55                  60

Ser Gly Arg Gly Cys Gly Ser Cys Phe Glu Ile Lys Cys Thr Lys Pro
 65                  70                  75                  80

Glu Ala Cys Ser Gly Glu Pro Val Val Val His Ile Thr Asp Asp Asn
                 85                  90                  95

Glu Glu Pro Ile Ala Ala Tyr His Phe Asp Leu Ser Gly Ile Ala Phe
            100                 105                 110

Gly Ser Met Ala Lys Lys Gly Asp Gln Lys Leu Arg Ser Ala Gly
            115                 120                 125

Glu Val Glu Ile Gln Phe Arg Arg Val Lys Cys Lys Tyr Pro Glu Gly
130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
                165                 170                 175

Asp Ile Lys Glu Lys Gly Lys Asp Lys Trp Ile Ala Leu Lys Glu Ser
            180                 185                 190

Trp Gly Ala Ile Trp Arg Ile Asp Thr Pro Glu Val Leu Lys Gly Pro
        195                 200                 205

Phe Thr Val Arg Tyr Thr Thr Glu Gly Gly Thr Lys Gly Glu Ala Lys
210                 215                 220

Asp Val Ile Pro Glu Gly Trp Lys Ala Asp Thr Ala Tyr Glu Ser Lys
225                 230                 235                 240
```

<210> SEQ ID NO 3
<211> LENGTH: 723
<212> TYPE: DNA
<213> ORGANISM: Phleum pratense
<220> FEATURE:
<221> NAME/KEY: CDS
<222> LOCATION: (1)..(720)

<400> SEQUENCE: 3

```
atc ccg aag gtc ccg ccg ggc ccg aac atc acg gcg acc tac ggc gac    48
Ile Pro Lys Val Pro Pro Gly Pro Asn Ile Thr Ala Thr Tyr Gly Asp
 1               5                  10                  15 aag tgg ctg gac gcg aag agc acc tgg tac ggc aag ccg acg gcc gcc    96
Lys Trp Leu Asp Ala Lys Ser Thr Trp Tyr Gly Lys Pro Thr Ala Ala
             20                  25                  30 ggt ccc aag gac aac ggc ggc gcg agc ggg tac aag gac gtg gac aag   144
Gly Pro Lys Asp Asn Gly Gly Ala Ser Gly Tyr Lys Asp Val Asp Lys
         35                  40                  45 ccc ccg ttc agc ggc atg acc ggc tcc ggc aac acc ccc atc ttc aag   192
Pro Pro Phe Ser Gly Met Thr Gly Ser Gly Asn Thr Pro Ile Phe Lys
 50                  55                  60 tcc ggc cgg ggc agc ggc tcc tcc ttc gag atc aag agc acc aag ccc   240
Ser Gly Arg Gly Ser Gly Ser Ser Phe Glu Ile Lys Ser Thr Lys Pro
 65                  70                  75                  80 gag gcc tcc tcc ggc gag ccc gtg gtg gtc cac atc acc gac gac aac   288
Glu Ala Ser Ser Gly Glu Pro Val Val Val His Ile Thr Asp Asp Asn
                 85                  90                  95 gag gag ccc atc gcc gcg tac cac ttc gac ctc tcc ggc atc gcg ttc   336
Glu Glu Pro Ile Ala Ala Tyr His Phe Asp Leu Ser Gly Ile Ala Phe
```

```
                           100                 105                  110
ggg tcc atg gcc aag aag ggc gac gag cag aag ctg cgc agc gcc ggc          384
Gly Ser Met Ala Lys Lys Gly Asp Glu Gln Lys Leu Arg Ser Ala Gly
        115                 120                 125 gag gtg gag atc cag ttc cgc cgc gtc aag tcc aag tac ccg gag ggc          432
Glu Val Glu Ile Gln Phe Arg Arg Val Lys Ser Lys Tyr Pro Glu Gly
130                 135                 140 acc aag gtg acc ttc cac gtg gag aag ggg tcc aac ccc aac tac ctg          480
Thr Lys Val Thr Phe His Val Glu Lys Gly Ser Asn Pro Asn Tyr Leu
145                 150                 155                 160 gcg ctg ctg gtg aag ttt gtc gcc ggc gac ggc gac gtg gtg gcg gtg          528
Ala Leu Leu Val Lys Phe Val Ala Gly Asp Gly Asp Val Val Ala Val
                165                 170                 175 gac atc aag gag aag ggc aag gac aag tgg atc gcg ctc aag gag tcg          576
Asp Ile Lys Glu Lys Gly Lys Asp Lys Trp Ile Ala Leu Lys Glu Ser
                180                 185                 190 tgg gga gcc atc tgg agg atc gac acc ccg gag gtg ctc aag ggc ccc          624
Trp Gly Ala Ile Trp Arg Ile Asp Thr Pro Glu Val Leu Lys Gly Pro
            195                 200                 205 ttc acc gtc cgc tac acc acc gag ggc ggc acc aag ggc gag gcc aag          672
Phe Thr Val Arg Tyr Thr Thr Glu Gly Gly Thr Lys Gly Glu Ala Lys
210                 215                 220 gac gtc atc ccc gag ggc tgg aag gcc gac acc gcc tac gag tcc aag          720
Asp Val Ile Pro Glu Gly Trp Lys Ala Asp Thr Ala Tyr Glu Ser Lys
225                 230                 235                 240 tga                                                                      723
```

<210> SEQ ID NO 4
<211> LENGTH: 240
<212> TYPE: PRT
<213> ORGANISM: Phleum pratense

<400> SEQUENCE: 4

```
Ile Pro Lys Val Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Ala Ala
                20                  25                  30

Gly Pro Lys Asp Asn Gly Gly Ala Ser Gly Tyr Lys Asp Val Asp Lys
            35                  40                  45

Pro Pro Phe Ser Gly Met Thr Gly Ser Gly Asn Thr Pro Ile Phe Lys
 50                  55                  60

Ser Gly Arg Gly Ser Gly Ser Ser Phe Glu Ile Lys Ser Thr Lys Pro
65                  70                  75                  80

Glu Ala Ser Ser Gly Glu Pro Val Val His Ile Thr Asp Asp Asn
                85                  90                  95

Glu Glu Pro Ile Ala Ala Tyr His Phe Asp Leu Ser Gly Ile Ala Phe
            100                 105                 110

Gly Ser Met Ala Lys Lys Gly Asp Glu Gln Lys Leu Arg Ser Ala Gly
        115                 120                 125

Glu Val Glu Ile Gln Phe Arg Arg Val Lys Ser Lys Tyr Pro Glu Gly
130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
                165                 170                 175

Asp Ile Lys Glu Lys Gly Lys Asp Lys Trp Ile Ala Leu Lys Glu Ser
                180                 185                 190
```

```
Trp Gly Ala Ile Trp Arg Ile Asp Thr Pro Glu Val Leu Lys Gly Pro
            195                 200                 205
Phe Thr Val Arg Tyr Thr Thr Glu Gly Gly Thr Lys Gly Glu Ala Lys
    210                 215                 220
Asp Val Ile Pro Glu Gly Trp Lys Ala Asp Thr Ala Tyr Glu Ser Lys
225                 230                 235                 240

<210> SEQ ID NO 5
<211> LENGTH: 705
<212> TYPE: DNA
<213> ORGANISM: Phleum pratense
<220> FEATURE:
<221> NAME/KEY: CDS
<222> LOCATION: (1)..(702)

<400> SEQUENCE: 5 ggc ccg aac atc acg gcg acc tac ggc gac aag tgg ctg gac gcg aag      48
Gly Pro Asn Ile Thr Ala Thr Tyr Gly Asp Lys Trp Leu Asp Ala Lys
  1               5                  10                  15 agc acc tgg tac ggc aag ccg acg gcc gcc ggt ccc aag gac aac ggc      96
Ser Thr Trp Tyr Gly Lys Pro Thr Ala Ala Gly Pro Lys Asp Asn Gly
             20                  25                  30 ggc gcg agc ggg tac aag gac gtg gac aag ccc ccg ttc agc ggc atg     144
Gly Ala Ser Gly Tyr Lys Asp Val Asp Lys Pro Pro Phe Ser Gly Met
         35                  40                  45 acc ggc tcc ggc aac acc ccc atc ttc aag tcc ggc cgg ggc agc ggc     192
Thr Gly Ser Gly Asn Thr Pro Ile Phe Lys Ser Gly Arg Gly Ser Gly
     50                  55                  60 tcc tcc ttc gag atc aag agc acc aag ccc gag gcc tcc tcc ggc gag     240
Ser Ser Phe Glu Ile Lys Ser Thr Lys Pro Glu Ala Ser Ser Gly Glu
 65                  70                  75                  80 ccc gtg gtg gtc cac atc acc gac gac aac gag gag ccc atc gcc gcg     288
Pro Val Val Val His Ile Thr Asp Asp Asn Glu Glu Pro Ile Ala Ala
                 85                  90                  95 tac cac ttc gac ctc tcc ggc atc gcg ttc ggg tcc atg gcc aag aag     336
Tyr His Phe Asp Leu Ser Gly Ile Ala Phe Gly Ser Met Ala Lys Lys
            100                 105                 110 ggc gac gag cag aag ctg cgc agc gcc ggc gag gtg gag atc cag ttc     384
Gly Asp Glu Gln Lys Leu Arg Ser Ala Gly Glu Val Glu Ile Gln Phe
        115                 120                 125 cgc cgc gtc aag tcc aag tac ccg gag ggc acc aag gtg acc ttc cac     432
Arg Arg Val Lys Ser Lys Tyr Pro Glu Gly Thr Lys Val Thr Phe His
    130                 135                 140 gtg gag aag ggg tcc aac ccc aac tac ctg gcg ctg ctg gtg aag ttt     480
Val Glu Lys Gly Ser Asn Pro Asn Tyr Leu Ala Leu Leu Val Lys Phe
145                 150                 155                 160 gtc gcc ggc gac ggc gac gtg gtg gcg gtg gac atc aag gag aag ggc     528
Val Ala Gly Asp Gly Asp Val Val Ala Val Asp Ile Lys Glu Lys Gly
                165                 170                 175 aag gac aag tgg atc gcg ctc aag gag tcg tgg gga gcc atc tgg agg     576
Lys Asp Lys Trp Ile Ala Leu Lys Glu Ser Trp Gly Ala Ile Trp Arg
            180                 185                 190 atc gac acc ccg gag gtg ctc aag ggc ccc ttc acc gtc cgc tac acc     624
Ile Asp Thr Pro Glu Val Leu Lys Gly Pro Phe Thr Val Arg Tyr Thr
        195                 200                 205 acc gag ggc ggc acc aag ggc gag gcc aag gac gtc atc ccc gag ggc     672
Thr Glu Gly Gly Thr Lys Gly Glu Ala Lys Asp Val Ile Pro Glu Gly
    210                 215                 220 tgg aag gcc gac acc gcc tac gag tcc aag tga                         705
Trp Lys Ala Asp Thr Ala Tyr Glu Ser Lys
225                 230
```

```
<210> SEQ ID NO 6
<211> LENGTH: 234
<212> TYPE: PRT
<213> ORGANISM: Phleum pratense

<400> SEQUENCE: 6

Gly Pro Asn Ile Thr Ala Thr Tyr Gly Asp Lys Trp Leu Asp Ala Lys
 1               5                  10                  15

Ser Thr Trp Tyr Gly Lys Pro Thr Ala Ala Gly Pro Lys Asp Asn Gly
            20                  25                  30

Gly Ala Ser Gly Tyr Lys Asp Val Asp Lys Pro Pro Phe Ser Gly Met
        35                  40                  45

Thr Gly Ser Gly Asn Thr Pro Ile Phe Lys Ser Gly Arg Gly Ser Gly
    50                  55                  60

Ser Ser Phe Glu Ile Lys Ser Thr Lys Pro Glu Ala Ser Ser Gly Glu
 65                  70                  75                  80

Pro Val Val Val His Ile Thr Asp Asp Asn Glu Glu Pro Ile Ala Ala
                85                  90                  95

Tyr His Phe Asp Leu Ser Gly Ile Ala Phe Gly Ser Met Ala Lys Lys
            100                 105                 110

Gly Asp Glu Gln Lys Leu Arg Ser Ala Gly Glu Val Glu Ile Gln Phe
        115                 120                 125

Arg Arg Val Lys Ser Lys Tyr Pro Glu Gly Thr Lys Val Thr Phe His
    130                 135                 140

Val Glu Lys Gly Ser Asn Pro Asn Tyr Leu Ala Leu Leu Val Lys Phe
145                 150                 155                 160

Val Ala Gly Asp Gly Asp Val Val Ala Val Asp Ile Lys Glu Lys Gly
                165                 170                 175

Lys Asp Lys Trp Ile Ala Leu Lys Glu Ser Trp Gly Ala Ile Trp Arg
            180                 185                 190

Ile Asp Thr Pro Glu Val Leu Lys Gly Pro Phe Thr Val Arg Tyr Thr
        195                 200                 205

Thr Glu Gly Gly Thr Lys Gly Glu Ala Lys Asp Val Ile Pro Glu Gly
    210                 215                 220

Trp Lys Ala Asp Thr Ala Tyr Glu Ser Lys
225                 230

<210> SEQ ID NO 7
<211> LENGTH: 633
<212> TYPE: DNA
<213> ORGANISM: Phleum pratense
<220> FEATURE:
<221> NAME/KEY: CDS
<222> LOCATION: (1)..(630)

<400> SEQUENCE: 7 gcc gcc ggt ccc aag gac aac ggc ggc gcg agc ggg tac aag gac gtg      48
Ala Ala Gly Pro Lys Asp Asn Gly Gly Ala Ser Gly Tyr Lys Asp Val
 1               5                  10                  15 gac aag ccc ccg ttc agc ggc atg acc ggc tcc ggc aac acc ccc atc      96
Asp Lys Pro Pro Phe Ser Gly Met Thr Gly Ser Gly Asn Thr Pro Ile
            20                  25                  30 ttc aag tcc ggc cgg ggc agc ggc tcc tcc ttc gag atc aag agc acc     144
Phe Lys Ser Gly Arg Gly Ser Gly Ser Ser Phe Glu Ile Lys Ser Thr
        35                  40                  45 aag ccc gag gcc tcc tcc ggc gag ccc gtg gtg gtc cac atc acc gac     192
Lys Pro Glu Ala Ser Ser Gly Glu Pro Val Val Val His Ile Thr Asp
    50                  55                  60
```

```
gac aac gag gag ccc atc gcc gcg tac cac ttc gac ctc tcc ggc atc         240
Asp Asn Glu Glu Pro Ile Ala Ala Tyr His Phe Asp Leu Ser Gly Ile
 65                  70                  75                  80 gcg ttc ggg tcc atg gcc aag aag ggc gac gag cag aag ctg cgc agc         288
Ala Phe Gly Ser Met Ala Lys Lys Gly Asp Glu Gln Lys Leu Arg Ser
                 85                  90                  95 gcc ggc gag gtg gag atc cag ttc cgc cgc gtc aag tcc aag tac ccg         336
Ala Gly Glu Val Glu Ile Gln Phe Arg Arg Val Lys Ser Lys Tyr Pro
            100                 105                 110 gag ggc acc aag gtg acc ttc cac gtg gag aag ggg tcc aac ccc aac         384
Glu Gly Thr Lys Val Thr Phe His Val Glu Lys Gly Ser Asn Pro Asn
        115                 120                 125 tac ctg gcg ctg ctg gtg aag ttt gtc gcc ggc gac ggc gac gtg gtg         432
Tyr Leu Ala Leu Leu Val Lys Phe Val Ala Gly Asp Gly Asp Val Val
130                 135                 140 gcg gtg gac atc aag gag aag ggc aag gac aag tgg atc gcg ctc aag         480
Ala Val Asp Ile Lys Glu Lys Gly Lys Asp Lys Trp Ile Ala Leu Lys
145                 150                 155                 160 gag tcg tgg gga gcc atc tgg agg atc gac acc ccg gag gtg ctc aag         528
Glu Ser Trp Gly Ala Ile Trp Arg Ile Asp Thr Pro Glu Val Leu Lys
                165                 170                 175 ggc ccc ttc acc gtc cgc tac acc acc gag ggc ggc acc aag ggc gag         576
Gly Pro Phe Thr Val Arg Tyr Thr Thr Glu Gly Gly Thr Lys Gly Glu
            180                 185                 190 gcc aag gac gtc atc ccc gag ggc tgg aag gcc gac acc gcc tac gag         624
Ala Lys Asp Val Ile Pro Glu Gly Trp Lys Ala Asp Thr Ala Tyr Glu
        195                 200                 205 tcc aag tga                                                              633
Ser Lys
    210

<210> SEQ ID NO 8
<211> LENGTH: 210
<212> TYPE: PRT
<213> ORGANISM: Phleum pratense

<400> SEQUENCE: 8

Ala Ala Gly Pro Lys Asp Asn Gly Gly Ala Ser Gly Tyr Lys Asp Val
  1               5                  10                  15

Asp Lys Pro Pro Phe Ser Gly Met Thr Gly Ser Gly Asn Thr Pro Ile
             20                  25                  30

Phe Lys Ser Gly Arg Gly Ser Gly Ser Ser Phe Glu Ile Lys Ser Thr
         35                  40                  45

Lys Pro Glu Ala Ser Ser Gly Glu Pro Val Val Val His Ile Thr Asp
     50                  55                  60

Asp Asn Glu Glu Pro Ile Ala Ala Tyr His Phe Asp Leu Ser Gly Ile
 65                  70                  75                  80

Ala Phe Gly Ser Met Ala Lys Lys Gly Asp Glu Gln Lys Leu Arg Ser
                 85                  90                  95

Ala Gly Glu Val Glu Ile Gln Phe Arg Arg Val Lys Ser Lys Tyr Pro
            100                 105                 110

Glu Gly Thr Lys Val Thr Phe His Val Glu Lys Gly Ser Asn Pro Asn
        115                 120                 125

Tyr Leu Ala Leu Leu Val Lys Phe Val Ala Gly Asp Gly Asp Val Val
130                 135                 140

Ala Val Asp Ile Lys Glu Lys Gly Lys Asp Lys Trp Ile Ala Leu Lys
145                 150                 155                 160

Glu Ser Trp Gly Ala Ile Trp Arg Ile Asp Thr Pro Glu Val Leu Lys
                165                 170                 175
```

```
Gly Pro Phe Thr Val Arg Tyr Thr Thr Glu Gly Gly Thr Lys Gly Glu
            180                 185                 190

Ala Lys Asp Val Ile Pro Glu Gly Trp Lys Ala Asp Thr Ala Tyr Glu
        195                 200                 205

Ser Lys
    210

<210> SEQ ID NO 9
<211> LENGTH: 684
<212> TYPE: DNA
<213> ORGANISM: Phleum pratense
<220> FEATURE:
<221> NAME/KEY: CDS
<222> LOCATION: (1)..(681)

<400> SEQUENCE: 9 atc ccg aag gtc ccg ccg ggc ccg aac atc acg gcg acc tac ggc gac      48
Ile Pro Lys Val Pro Pro Gly Pro Asn Ile Thr Ala Thr Tyr Gly Asp
  1               5                  10                  15 aag tgg ctg gac gcg aag agc acc tgg tac ggc aag ccg acg gcc gcc      96
Lys Trp Leu Asp Ala Lys Ser Thr Trp Tyr Gly Lys Pro Thr Ala Ala
             20                  25                  30 ggt ccc aag gac aac ggc ggc gcg agc ggg tac aag gac gtg gac aag     144
Gly Pro Lys Asp Asn Gly Gly Ala Ser Gly Tyr Lys Asp Val Asp Lys
         35                  40                  45 ccc ccg ttc agc ggc atg acc ggc tcc ggc aac acc ccc atc ttc aag     192
Pro Pro Phe Ser Gly Met Thr Gly Ser Gly Asn Thr Pro Ile Phe Lys
     50                  55                  60 tcc ggc cgg ggc agc ggc tcc tcc ttc gag atc aag agc acc aag ccc     240
Ser Gly Arg Gly Ser Gly Ser Ser Phe Glu Ile Lys Ser Thr Lys Pro
 65                  70                  75                  80 gag gcc tcc tcc ggc gag ccc gtg gtg gtc cac ttc gac ctc tcc ggc     288
Glu Ala Ser Ser Gly Glu Pro Val Val Val His Phe Asp Leu Ser Gly
                 85                  90                  95 atc gcg ttc ggg tcc atg gcc aag aag ggc gac gag cag aag ctg cgc     336
Ile Ala Phe Gly Ser Met Ala Lys Lys Gly Asp Glu Gln Lys Leu Arg
            100                 105                 110 agc gcc ggc gag gtg gag atc cag ttc cgc cgc gtc aag tcc aag tac     384
Ser Ala Gly Glu Val Glu Ile Gln Phe Arg Arg Val Lys Ser Lys Tyr
        115                 120                 125 ccg gag ggc acc aag gtg acc ttc cac gtg gag aag ggg tcc aac ccc     432
Pro Glu Gly Thr Lys Val Thr Phe His Val Glu Lys Gly Ser Asn Pro
    130                 135                 140 aac tac ctg gcg ctg ctg gtg aag ttt gtc gcc ggc gac ggc gac gtg     480
Asn Tyr Leu Ala Leu Leu Val Lys Phe Val Ala Gly Asp Gly Asp Val
145                 150                 155                 160 gtg gcg gtg gac atc aag gag aag ggc aag gac aag tgg atc gcg ctc     528
Val Ala Val Asp Ile Lys Glu Lys Gly Lys Asp Lys Trp Ile Ala Leu
                165                 170                 175 aag gag tcg tgg gga gcc atc tgg agg atc gac acc ccg gag gtg ctc     576
Lys Glu Ser Trp Gly Ala Ile Trp Arg Ile Asp Thr Pro Glu Val Leu
            180                 185                 190 aag ggc ccc ttc acc gtc cgc tac acc acc gag ggc ggc acc aag ggc     624
Lys Gly Pro Phe Thr Val Arg Tyr Thr Thr Glu Gly Gly Thr Lys Gly
        195                 200                 205 gag gcc aag gac gtc atc ccc gag ggc tgg aag gcc gac acc gcc tac     672
Glu Ala Lys Asp Val Ile Pro Glu Gly Trp Lys Ala Asp Thr Ala Tyr
    210                 215                 220 gag tcc aag tga                                                     684
Glu Ser Lys
225
```

<210> SEQ ID NO 10
<211> LENGTH: 227
<212> TYPE: PRT
<213> ORGANISM: Phleum pratense

<400> SEQUENCE: 10

```
Ile Pro Lys Val Pro Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Ala Ala
            20                  25                  30

Gly Pro Lys Asp Asn Gly Gly Ala Ser Gly Tyr Lys Asp Val Asp Lys
        35                  40                  45

Pro Pro Phe Ser Gly Met Thr Gly Ser Gly Asn Thr Pro Ile Phe Lys
    50                  55                  60

Ser Gly Arg Gly Ser Gly Ser Phe Glu Ile Lys Ser Thr Lys Pro
 65                  70                  75                  80

Glu Ala Ser Ser Gly Glu Pro Val Val Val His Phe Asp Leu Ser Gly
                85                  90                  95

Ile Ala Phe Gly Ser Met Ala Lys Lys Gly Asp Glu Gln Lys Leu Arg
            100                 105                 110

Ser Ala Gly Glu Val Glu Ile Gln Phe Arg Arg Val Lys Ser Lys Tyr
        115                 120                 125

Pro Glu Gly Thr Lys Val Thr Phe His Val Glu Lys Gly Ser Asn Pro
    130                 135                 140

Asn Tyr Leu Ala Leu Leu Val Lys Phe Val Ala Gly Asp Gly Asp Val
145                 150                 155                 160

Val Ala Val Asp Ile Lys Glu Lys Gly Lys Asp Lys Trp Ile Ala Leu
                165                 170                 175

Lys Glu Ser Trp Gly Ala Ile Trp Arg Ile Asp Thr Pro Glu Val Leu
            180                 185                 190

Lys Gly Pro Phe Thr Val Arg Tyr Thr Thr Glu Gly Thr Lys Gly
        195                 200                 205

Glu Ala Lys Asp Val Ile Pro Glu Gly Trp Lys Ala Asp Thr Ala Tyr
    210                 215                 220

Glu Ser Lys
225
```

<210> SEQ ID NO 11
<211> LENGTH: 708
<212> TYPE: DNA
<213> ORGANISM: Phleum pratense
<220> FEATURE:
<221> NAME/KEY: CDS
<222> LOCATION: (1)..(705)

<400> SEQUENCE: 11

```
atc ccg aag gtc ccg ccg ggc ccg aac atc acg gcg acc tac ggc gac    48
Ile Pro Lys Val Pro Pro Gly Pro Asn Ile Thr Ala Thr Tyr Gly Asp
 1               5                  10                  15 aag tgg ctg gac gcg aag agc acc tgg tac ggc aag ccg acg gcc gcc    96
Lys Trp Leu Asp Ala Lys Ser Thr Trp Tyr Gly Lys Pro Thr Ala Ala
            20                  25                  30 ggt ccc aag gac aac ggc ggc gcg agc ggg tac aag gac gtg gac aag   144
Gly Pro Lys Asp Asn Gly Gly Ala Ser Gly Tyr Lys Asp Val Asp Lys
        35                  40                  45 ccc ccg ttc agc ggc atg acc ggc tcc ggc aac acc ccc atc ttc aag   192
Pro Pro Phe Ser Gly Met Thr Gly Ser Gly Asn Thr Pro Ile Phe Lys
    50                  55                  60
```

```
tcc ggc cgg ggc agc ggc tcc tcc ttc gag atc aag agc acc aag ccc      240
Ser Gly Arg Gly Ser Gly Ser Ser Phe Glu Ile Lys Ser Thr Lys Pro
 65                  70                  75                  80 gag gcc tcc tcc ggc gag ccc gtg gtg gtc cac atc acc gac gac aac      288
Glu Ala Ser Ser Gly Glu Pro Val Val Val His Ile Thr Asp Asp Asn
             85                  90                  95 gag gag ccc atc gcc gcg tac cac ttc gac ctc tcc ggc atc gcg ttc      336
Glu Glu Pro Ile Ala Ala Tyr His Phe Asp Leu Ser Gly Ile Ala Phe
         100                 105                 110 ggg tcc gac gag cag aag ctg cgc agc gcc ggc gag gtg gag atc cag      384
Gly Ser Asp Glu Gln Lys Leu Arg Ser Ala Gly Glu Val Glu Ile Gln
     115                 120                 125 ttc cgc cgc gtc aag tcc aag tac ccg gag ggc acc aag gtg acc ttc      432
Phe Arg Arg Val Lys Ser Lys Tyr Pro Glu Gly Thr Lys Val Thr Phe
130                 135                 140 cac gtg gag aag ggg tcc aac ccc aac tac ctg gcg ctg ctg gtg aag      480
His Val Glu Lys Gly Ser Asn Pro Asn Tyr Leu Ala Leu Leu Val Lys
145                 150                 155                 160 ttt gtc gcc ggc gac ggc gac gtg gtg gcg gtg gac atc aag gag aag      528
Phe Val Ala Gly Asp Gly Asp Val Val Ala Val Asp Ile Lys Glu Lys
                165                 170                 175 ggc aag gac aag tgg atc gcg ctc aag gag tcg tgg gga gcc atc tgg      576
Gly Lys Asp Lys Trp Ile Ala Leu Lys Glu Ser Trp Gly Ala Ile Trp
            180                 185                 190 agg atc gac acc ccg gag gtg ctc aag ggc ccc ttc acc gtc cgc tac      624
Arg Ile Asp Thr Pro Glu Val Leu Lys Gly Pro Phe Thr Val Arg Tyr
        195                 200                 205 acc acc gag ggc ggc acc aag ggc gag gcc aag gac gtc atc ccc gag      672
Thr Thr Glu Gly Gly Thr Lys Gly Glu Ala Lys Asp Val Ile Pro Glu
    210                 215                 220 ggc tgg aag gcc gac acc gcc tac gag tcc aag tga                      708
Gly Trp Lys Ala Asp Thr Ala Tyr Glu Ser Lys
225                 230                 235

<210> SEQ ID NO 12
<211> LENGTH: 235
<212> TYPE: PRT
<213> ORGANISM: Phleum pratense

<400> SEQUENCE: 12

Ile Pro Lys Val Pro Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Ala Ala
            20                  25                  30

Gly Pro Lys Asp Asn Gly Gly Ala Ser Gly Tyr Lys Asp Val Asp Lys
        35                  40                  45

Pro Pro Phe Ser Gly Met Thr Gly Ser Gly Asn Thr Pro Ile Phe Lys
    50                  55                  60

Ser Gly Arg Gly Ser Gly Ser Ser Phe Glu Ile Lys Ser Thr Lys Pro
 65                 70                  75                  80

Glu Ala Ser Ser Gly Glu Pro Val Val Val His Ile Thr Asp Asp Asn
             85                  90                  95

Glu Glu Pro Ile Ala Ala Tyr His Phe Asp Leu Ser Gly Ile Ala Phe
         100                 105                 110

Gly Ser Asp Glu Gln Lys Leu Arg Ser Ala Gly Glu Val Glu Ile Gln
     115                 120                 125

Phe Arg Arg Val Lys Ser Lys Tyr Pro Glu Gly Thr Lys Val Thr Phe
130                 135                 140
```

```
His Val Glu Lys Gly Ser Asn Pro Asn Tyr Leu Ala Leu Leu Val Lys
145                 150                 155                 160

Phe Val Ala Gly Asp Gly Asp Val Val Ala Val Asp Ile Lys Glu Lys
                165                 170                 175

Gly Lys Asp Lys Trp Ile Ala Leu Lys Glu Ser Trp Gly Ala Ile Trp
            180                 185                 190

Arg Ile Asp Thr Pro Glu Val Leu Lys Gly Pro Phe Thr Val Arg Tyr
        195                 200                 205

Thr Thr Glu Gly Gly Thr Lys Gly Glu Ala Lys Asp Val Ile Pro Glu
    210                 215                 220

Gly Trp Lys Ala Asp Thr Ala Tyr Glu Ser Lys
225                 230                 235

<210> SEQ ID NO 13
<211> LENGTH: 690
<212> TYPE: DNA
<213> ORGANISM: Phleum pratense
<220> FEATURE:
<221> NAME/KEY: CDS
<222> LOCATION: (1)..(687)

<400> SEQUENCE: 13 atc ccg aag gtc ccg ccg ggc ccg aac atc acg gcg acc tac ggc gac      48
Ile Pro Lys Val Pro Pro Gly Pro Asn Ile Thr Ala Thr Tyr Gly Asp
1               5                   10                  15 aag tgg ctg gac gcg aag agc acc tgg tac ggc aag ccg acg gcc gcc      96
Lys Trp Leu Asp Ala Lys Ser Thr Trp Tyr Gly Lys Pro Thr Ala Ala
                20                  25                  30 ggt ccc aag gac aac ggc ggc gcg agc ggg tac aag gac gtg gac aag     144
Gly Pro Lys Asp Asn Gly Gly Ala Ser Gly Tyr Lys Asp Val Asp Lys
            35                  40                  45 ccc ccg ttc agc ggc atg acc ggc tcc ggc aac acc ccc atc ttc aag     192
Pro Pro Phe Ser Gly Met Thr Gly Ser Gly Asn Thr Pro Ile Phe Lys
        50                  55                  60 tcc ggc cgg ggc agc ggc tcc tcc ttc gag atc aag agc acc aag ccc     240
Ser Gly Arg Gly Ser Gly Ser Ser Phe Glu Ile Lys Ser Thr Lys Pro
65                  70                  75                  80 gag gcc tcc tcc ggc gag ccc gtg gtg gtc cac atc acc gac gac aac     288
Glu Ala Ser Ser Gly Glu Pro Val Val Val His Ile Thr Asp Asp Asn
                85                  90                  95 gag gag ccc atc gcc gcg tac cac ttc gac ctc tcc ggc atc gcg ttc     336
Glu Glu Pro Ile Ala Ala Tyr His Phe Asp Leu Ser Gly Ile Ala Phe
            100                 105                 110 ggg tcc atg gcc aag aag ggc gac gag cag aag ctg cgc agc gcc ggc     384
Gly Ser Met Ala Lys Lys Gly Asp Glu Gln Lys Leu Arg Ser Ala Gly
        115                 120                 125 gag gtg gag atc cag ttc cgc cgc gtc aag tcc aag tac ccg gag ggc     432
Glu Val Glu Ile Gln Phe Arg Arg Val Lys Ser Lys Tyr Pro Glu Gly
130                 135                 140 acc aag gtg acc ttc cac gtg gag aag ggg tcc aac ccc aac tac ctg     480
Thr Lys Val Thr Phe His Val Glu Lys Gly Ser Asn Pro Asn Tyr Leu
145                 150                 155                 160 gcg ctg ctg gtg aag ttt gtc gcc ggc gac ggc gac gtg gtg tgg atc     528
Ala Leu Leu Val Lys Phe Val Ala Gly Asp Gly Asp Val Val Trp Ile
                165                 170                 175 gcg ctc aag gag tcg tgg gga gcc atc tgg agg atc gac acc ccg gag     576
Ala Leu Lys Glu Ser Trp Gly Ala Ile Trp Arg Ile Asp Thr Pro Glu
            180                 185                 190 gtg ctc aag ggc ccc ttc acc gtc cgc tac acc acc gag ggc ggc acc     624
Val Leu Lys Gly Pro Phe Thr Val Arg Tyr Thr Thr Glu Gly Gly Thr
        195                 200                 205
```

| | | |
|---|---|---|
| aag ggc gag gcc aag gac gtc atc ccc gag ggc tgg aag gcc gac acc | | 672 |
| Lys Gly Glu Ala Lys Asp Val Ile Pro Glu Gly Trp Lys Ala Asp Thr | | |
| 210 215 220 | | |
| | | |
| gcc tac gag tcc aag tga | | 690 |
| Ala Tyr Glu Ser Lys | | |
| 225 | | |

<210> SEQ ID NO 14
<211> LENGTH: 229
<212> TYPE: PRT
<213> ORGANISM: Phleum pratense

<400> SEQUENCE: 14

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Ala Ala
            20                  25                  30

Gly Pro Lys Asp Asn Gly Gly Ala Ser Gly Tyr Lys Asp Val Asp Lys
        35                  40                  45

Pro Pro Phe Ser Gly Met Thr Gly Ser Gly Asn Thr Pro Ile Phe Lys
    50                  55                  60

Ser Gly Arg Gly Ser Gly Ser Ser Phe Glu Ile Lys Ser Thr Lys Pro
65                  70                  75                  80

Glu Ala Ser Ser Gly Glu Pro Val Val His Ile Thr Asp Asp Asn
                85                  90                  95

Glu Glu Pro Ile Ala Ala Tyr His Phe Asp Leu Ser Gly Ile Ala Phe
            100                 105                 110

Gly Ser Met Ala Lys Lys Gly Asp Glu Gln Lys Leu Arg Ser Ala Gly
        115                 120                 125

Glu Val Glu Ile Gln Phe Arg Arg Val Lys Ser Lys Tyr Pro Glu Gly
130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Trp Ile
                165                 170                 175

Ala Leu Lys Glu Ser Trp Gly Ala Ile Trp Arg Ile Asp Thr Pro Glu
            180                 185                 190

Val Leu Lys Gly Pro Phe Thr Val Arg Tyr Thr Thr Glu Gly Gly Thr
        195                 200                 205

Lys Gly Glu Ala Lys Asp Val Ile Pro Glu Gly Trp Lys Ala Asp Thr
210                 215                 220

Ala Tyr Glu Ser Lys
225

<210> SEQ ID NO 15
<211> LENGTH: 699
<212> TYPE: DNA
<213> ORGANISM: Phleum pratense
<220> FEATURE:
<221> NAME/KEY: CDS
<222> LOCATION: (1)..(696)

<400> SEQUENCE: 15

| | | |
|---|---|---|
| atc ccg aag gtc ccg ccg ggc ccg aac atc acg gcg acc tac ggc gac | | 48 |
| Ile Pro Lys Val Pro Pro Gly Pro Asn Ile Thr Ala Thr Tyr Gly Asp | | |
| 1               5                   10                  15 | | |
| | | |
| aag tgg ctg gac gcg aag agc acc tgg tac ggc aag ccg acg gcc gcc | | 96 |
| Lys Trp Leu Asp Ala Lys Ser Thr Trp Tyr Gly Lys Pro Thr Ala Ala | | |
| 20                  25                  30 | | |

```
ggt ccc aag gac aac ggc ggc gcg agc ggg tac aag gac gtg gac aag      144
Gly Pro Lys Asp Asn Gly Gly Ala Ser Gly Tyr Lys Asp Val Asp Lys
         35                  40                  45 ccc ccg ttc agc ggc atg acc ggc tcc ggc aac acc ccc atc ttc aag      192
Pro Pro Phe Ser Gly Met Thr Gly Ser Gly Asn Thr Pro Ile Phe Lys
 50                  55                  60 tcc ggc cgg ggc agc ggc tcc tcc ttc gag atc aag agc acc aag ccc      240
Ser Gly Arg Gly Ser Gly Ser Ser Phe Glu Ile Lys Ser Thr Lys Pro
 65                  70                  75                  80 gag gcc tcc tcc ggc gag ccc gtg gtg gtc cac atc acc gac gac aac      288
Glu Ala Ser Ser Gly Glu Pro Val Val Val His Ile Thr Asp Asp Asn
                 85                  90                  95 gag gag ccc atc gcc gcg tac cac ttc gac ctc tcc ggc atc gcg ttc      336
Glu Glu Pro Ile Ala Ala Tyr His Phe Asp Leu Ser Gly Ile Ala Phe
             100                 105                 110 ggg tcc atg gcc aag aag ggc gac gag cag aag ctg cgc agc gcc ggc      384
Gly Ser Met Ala Lys Lys Gly Asp Glu Gln Lys Leu Arg Ser Ala Gly
         115                 120                 125 gag gtg gag atc cag ttc cgc cgc gtc aag tcc aag tac ccg gag ggc      432
Glu Val Glu Ile Gln Phe Arg Arg Val Lys Ser Lys Tyr Pro Glu Gly
130                 135                 140 acc aag gtg acc ttc cac gtg gag aag ggg tcc aac ccc aac tac ctg      480
Thr Lys Val Thr Phe His Val Glu Lys Gly Ser Asn Pro Asn Tyr Leu
145                 150                 155                 160 gcg ctg ctg gtg aag ttt gtc gcc ggc gac ggc gac gtg gtg gcg gtg      528
Ala Leu Leu Val Lys Phe Val Ala Gly Asp Gly Asp Val Val Ala Val
                165                 170                 175 gac atc aag gag aag ggc aag gac aag tgg atc gcg ctc aag gag tcg      576
Asp Ile Lys Glu Lys Gly Lys Asp Lys Trp Ile Ala Leu Lys Glu Ser
            180                 185                 190 tgg gga gcc atc tgg agg atc gac acc ccg gag gtg ctc aag ggc ccc      624
Trp Gly Ala Ile Trp Arg Ile Asp Thr Pro Glu Val Leu Lys Gly Pro
        195                 200                 205 ttc acc gtc cgc ggc gag gcc aag gac gtc atc ccc gag ggc tgg aag      672
Phe Thr Val Arg Gly Glu Ala Lys Asp Val Ile Pro Glu Gly Trp Lys
210                 215                 220 gcc gac acc gcc tac gag tcc aag tga                                  699
Ala Asp Thr Ala Tyr Glu Ser Lys
225                 230
```

<210> SEQ ID NO 16
<211> LENGTH: 232
<212> TYPE: PRT
<213> ORGANISM: Phleum pratense

<400> SEQUENCE: 16

```
Ile Pro Lys Val Pro Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Ala Ala
             20                  25                  30

Gly Pro Lys Asp Asn Gly Gly Ala Ser Gly Tyr Lys Asp Val Asp Lys
         35                  40                  45

Pro Pro Phe Ser Gly Met Thr Gly Ser Gly Asn Thr Pro Ile Phe Lys
 50                  55                  60

Ser Gly Arg Gly Ser Gly Ser Ser Phe Glu Ile Lys Ser Thr Lys Pro
 65                  70                  75                  80

Glu Ala Ser Ser Gly Glu Pro Val Val Val His Ile Thr Asp Asp Asn
                 85                  90                  95

Glu Glu Pro Ile Ala Ala Tyr His Phe Asp Leu Ser Gly Ile Ala Phe
```

```
                100                 105                 110
Gly Ser Met Ala Lys Lys Gly Asp Glu Gln Lys Leu Arg Ser Ala Gly
            115                 120                 125

Glu Val Glu Ile Gln Phe Arg Arg Val Lys Ser Lys Tyr Pro Glu Gly
            130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
                165                 170                 175

Asp Ile Lys Glu Lys Gly Lys Asp Lys Trp Ile Ala Leu Lys Glu Ser
            180                 185                 190

Trp Gly Ala Ile Trp Arg Ile Asp Thr Pro Glu Val Leu Lys Gly Pro
            195                 200                 205

Phe Thr Val Arg Gly Glu Ala Lys Asp Val Ile Pro Glu Gly Trp Lys
            210                 215                 220

Ala Asp Thr Ala Tyr Glu Ser Lys
225                 230

<210> SEQ ID NO 17
<211> LENGTH: 666
<212> TYPE: DNA
<213> ORGANISM: Phleum pratense
<220> FEATURE:
<221> NAME/KEY: CDS
<222> LOCATION: (1)..(663)

<400> SEQUENCE: 17 ggc ccg aac atc acg gcg acc tac ggc gac aag tgg ctg gac gcg aag      48
Gly Pro Asn Ile Thr Ala Thr Tyr Gly Asp Lys Trp Leu Asp Ala Lys
 1               5                  10                  15 agc acc tgg tac ggc aag ccg acg gcc gcc ggt ccc aag gac aac ggc      96
Ser Thr Trp Tyr Gly Lys Pro Thr Ala Ala Gly Pro Lys Asp Asn Gly
            20                  25                  30 ggc gcg agc ggg tac aag gac gtg gac aag ccc ccg ttc agc ggc atg     144
Gly Ala Ser Gly Tyr Lys Asp Val Asp Lys Pro Pro Phe Ser Gly Met
        35                  40                  45 acc ggc tcc ggc aac acc ccc atc ttc aag tcc ggc cgg ggc agc ggc     192
Thr Gly Ser Gly Asn Thr Pro Ile Phe Lys Ser Gly Arg Gly Ser Gly
    50                  55                  60 tcc tcc ttc gag atc aag agc acc aag ccc gag gcc tcc tcc ggc gag     240
Ser Ser Phe Glu Ile Lys Ser Thr Lys Pro Glu Ala Ser Ser Gly Glu
65                  70                  75                  80 ccc gtg gtg gtc cac atc acc gac gac aac gag gag ccc atc gcc gcg     288
Pro Val Val Val His Ile Thr Asp Asp Asn Glu Glu Pro Ile Ala Ala
                85                  90                  95 tac cac ttc gac ctc tcc ggc atc gcg ttc ggg tcc gac gag cag aag     336
Tyr His Phe Asp Leu Ser Gly Ile Ala Phe Gly Ser Asp Glu Gln Lys
            100                 105                 110 ctg cgc agc gcc ggc gag gtg gag atc cag ttc cgc cgc gtc aag tcc     384
Leu Arg Ser Ala Gly Glu Val Glu Ile Gln Phe Arg Arg Val Lys Ser
        115                 120                 125 aag tac ccg gag ggc acc aag gtg acc ttc cac gtg gag aag ggg tcc     432
Lys Tyr Pro Glu Gly Thr Lys Val Thr Phe His Val Glu Lys Gly Ser
    130                 135                 140 aac ccc aac tac ctg gcg ctg ctg gtg aag ttt gtc gcc ggc gac ggc     480
Asn Pro Asn Tyr Leu Ala Leu Leu Val Lys Phe Val Ala Gly Asp Gly
145                 150                 155                 160 gac gtg gtg gcg gtg gac atc aag gag aag ggc aag gac aag tgg atc     528
Asp Val Val Ala Val Asp Ile Lys Glu Lys Gly Lys Asp Lys Trp Ile
                165                 170                 175
```

```
gcg ctc aag gag tcg tgg gga gcc atc tgg agg atc gac acc ccg gag    576
Ala Leu Lys Glu Ser Trp Gly Ala Ile Trp Arg Ile Asp Thr Pro Glu
        180                 185                 190 gtg ctc aag ggc ccc ttc acc gtc cgc ggc gag gcc aag gac gtc atc    624
Val Leu Lys Gly Pro Phe Thr Val Arg Gly Glu Ala Lys Asp Val Ile
        195                 200                 205 ccc gag ggc tgg aag gcc gac acc gcc tac gag tcc aag tga            666
Pro Glu Gly Trp Lys Ala Asp Thr Ala Tyr Glu Ser Lys
210                 215                 220
```

<210> SEQ ID NO 18
<211> LENGTH: 221
<212> TYPE: PRT
<213> ORGANISM: Phleum pratense

<400> SEQUENCE: 18

```
Gly Pro Asn Ile Thr Ala Thr Tyr Gly Asp Lys Trp Leu Asp Ala Lys
1               5                   10                  15

Ser Thr Trp Tyr Gly Lys Pro Thr Ala Gly Pro Lys Asp Asn Gly
            20                  25                  30

Gly Ala Ser Gly Tyr Lys Asp Val Asp Lys Pro Pro Phe Ser Gly Met
        35                  40                  45

Thr Gly Ser Gly Asn Thr Pro Ile Phe Lys Ser Gly Arg Gly Ser Gly
    50                  55                  60

Ser Ser Phe Glu Ile Lys Ser Thr Lys Pro Glu Ala Ser Ser Gly Glu
                65                  70                  75              80

Pro Val Val Val His Ile Thr Asp Asp Asn Glu Glu Pro Ile Ala Ala
                85                  90                  95

Tyr His Phe Asp Leu Ser Gly Ile Ala Phe Gly Ser Asp Glu Gln Lys
            100                 105                 110

Leu Arg Ser Ala Gly Glu Val Glu Ile Gln Phe Arg Arg Val Lys Ser
        115                 120                 125

Lys Tyr Pro Glu Gly Thr Lys Val Thr Phe His Val Glu Lys Gly Ser
130                 135                 140

Asn Pro Asn Tyr Leu Ala Leu Leu Val Lys Phe Val Ala Gly Asp Gly
                145                 150                 155             160

Asp Val Val Ala Val Asp Ile Lys Glu Lys Gly Lys Asp Lys Trp Ile
            165                 170                 175

Ala Leu Lys Glu Ser Trp Gly Ala Ile Trp Arg Ile Asp Thr Pro Glu
        180                 185                 190

Val Leu Lys Gly Pro Phe Thr Val Arg Gly Glu Ala Lys Asp Val Ile
    195                 200                 205

Pro Glu Gly Trp Lys Ala Asp Thr Ala Tyr Glu Ser Lys
210                 215                 220
```

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
atcccgaagg tcccgccg                                                18

<210> SEQ ID NO 20
<211> LENGTH: 63
<212> TYPE: DNA

-continued

<213> ORGANISM: Artificial Sequence
<220> FEATURE:
<223> OTHER INFORMATION: Description of Artificial Sequence: Synthetic
      primer

<400> SEQUENCE: 20
atcccgaagg tcccgccggg cccgaacatc acggcgacct acggcgacaa gtggctggac    60
gcg                                                                  63

<210> SEQ ID NO 21
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gttgtccttg gaccggcgg ccgtcggctt gccgtaccag gtgctcttcg cgtccagcca    60
ctt                                                                  63

<210> SEQ ID NO 22
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtcccaagg acaacggcgg cgcgagcggg tacaaggacg tggacaagcc cccgttcagc    60
gg                                                                   62

<210> SEQ ID NO 23
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gagccgctgc cccggccgga cttgaagatg ggggtgttgc cggagccggt catgccgctg    60
aacggggggc                                                           69

<210> SEQ ID NO 24
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccggccggg gcagcggctc ctccttcgag atcaagagca ccaagcccga ggcctcctcc    60
ggcgagccc                                                            69

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
ggtaagcttt cacttggact cgtaggcggt                                      30

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccgggtact tggacttgac gcg                                             23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcgtcaagt ccaagtaccc gga                                             23

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgaacatca cggcgaccta cggcgacaag tggctggacg cg                        42

<210> SEQ ID NO 29
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtcgaagtgg tacgcggcga tgggctcctc gttgtcgtcg gtgatgtgga ccaccacggg     60
ctcgccgga                                                             69

<210> SEQ ID NO 30
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gccgcgtacc acttcgacct ctccggcatc gcgttcgggt ccgacgagca gaagctgcgc     60
agcgccggc                                                             69

<210> SEQ ID NO 31
<211> LENGTH: 96
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 31
ggtaagcttt cacttggact cgtaggcggt gtcggccttc agccctcgg ggatgacgtc    60 cttggcctcg ccgcggacgg tgaagggggcc cttgag    96

<210> SEQ ID NO 32
<211> LENGTH: 240
<212> TYPE: PRT
<213> ORGANISM: Phleum pratense

<400> SEQUENCE: 32

```
Ile Pro Lys Val Pro Pro Gly Pro Asn Ile Thr Ala Thr Tyr Gly Asp
 1               5                   10                  15

Lys Trp Leu Asp Ala Lys Ser Thr Trp Tyr Gly Lys Pro Thr Ala Ala
            20                  25                  30

Gly Pro Lys Asp Asn Gly Gly Ala Cys Gly Tyr Lys Asp Val Asp Lys
        35                  40                  45

Pro Pro Phe Ser Gly Met Thr Gly Cys Gly Asn Thr Pro Ile Phe Lys
    50                  55                  60

Ser Gly Arg Gly Cys Gly Ser Cys Phe Glu Ile Lys Cys Thr Lys Pro
65                  70                  75                  80

Glu Ala Cys Ser Gly Glu Pro Val Val Val His Ile Thr Asp Asp Asn
                85                  90                  95

Glu Glu Pro Ile Ala Ala Tyr His Phe Asp Leu Ser Gly Ile Ala Phe
            100                 105                 110

Gly Ser Met Ala Lys Lys Gly Asp Glu Gln Lys Leu Arg Ser Ala Gly
        115                 120                 125

Glu Val Glu Ile Gln Phe Arg Arg Val Lys Cys Lys Tyr Pro Glu Gly
    130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
                165                 170                 175

Asp Ile Lys Glu Lys Gly Lys Asp Lys Trp Ile Ala Leu Lys Glu Ser
            180                 185                 190

Trp Gly Ala Ile Trp Arg Ile Asp Thr Pro Glu Val Leu Lys Gly Pro
        195                 200                 205

Phe Thr Val Arg Tyr Thr Thr Glu Gly Gly Thr Lys Gly Glu Ala Lys
    210                 215                 220

Asp Val Ile Pro Glu Gly Trp Lys Ala Asp Thr Ala Tyr Glu Ser Lys
225                 230                 235                 240
```

<210> SEQ ID NO 33
<211> LENGTH: 240
<212> TYPE: PRT
<213> ORGANISM: Poa pratensis

<400> SEQUENCE: 33

```
Ile Ala Lys Val Pro Pro Gly Pro Asn Ile Thr Ala Thr Tyr Gly Asp
 1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
        35                  40                  45

Ala Pro Phe Ser Gly Met Thr Gly Cys Gly Asn Thr Pro Ile Phe Lys
    50                  55                  60
```

Ser Gly Arg Gly Cys Gly Ser Cys Phe Glu Ile Lys Cys Thr Lys Pro
65                  70                  75                  80

Glu Ser Cys Ser Gly Glu Pro Val Leu Val His Ile Thr Asp Asp Asn
            85                  90                  95

Glu Glu Pro Ile Ala Ala Tyr His Phe Asp Leu Ser Gly Lys Ala Phe
        100                 105                 110

Gly Ala Met Ala Lys Lys Gly Glu Glu Gln Lys Leu Arg Ser Ala Gly
        115                 120                 125

Glu Leu Glu Leu Lys Phe Arg Arg Val Lys Cys Glu Tyr Pro Glu Gly
    130                 135                 140

Thr Lys Val Thr Phe His Val Glu Lys Gly Ser Asn Pro Asn Tyr Leu
145                 150                 155                 160

Ala Leu Leu Val Lys Tyr Val Thr Gly Asp Gly Asp Val Val Ala Val
                165                 170                 175

Asp Ile Lys Glu Lys Gly Lys Asp Lys Trp Ile Glu Leu Lys Glu Ser
            180                 185                 190

Trp Gly Ser Ile Trp Arg Val Asp Thr Pro Asp Lys Leu Thr Gly Pro
        195                 200                 205

Phe Thr Val Arg Tyr Thr Thr Glu Gly Gly Thr Lys Gly Glu Ala Glu
    210                 215                 220

Asp Val Ile Pro Glu Gly Trp Lys Ala Asp Thr Ala Tyr Ala Ser Lys
225                 230                 235                 240

<210> SEQ ID NO 34
<211> LENGTH: 240
<212> TYPE: PRT
<213> ORGANISM: Holcus lanatus

<400> SEQUENCE: 34

Ile Ala Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
        35                  40                  45

Pro Pro Phe Ser Gly Met Thr Gly Cys Gly Asn Thr Pro Ile Phe Lys
    50                  55                  60

Ser Gly Arg Gly Cys Gly Ser Cys Phe Glu Ile Lys Cys Thr Lys Pro
65                  70                  75                  80

Glu Ser Cys Ser Gly Glu Pro Ile Val Val His Ile Thr Asp Asp Asn
            85                  90                  95

Glu Glu Pro Ile Ala Ala Tyr His Leu Asp Leu Ser Gly Lys Ala Phe
        100                 105                 110

Gly Ala Met Ala Lys Lys Gly Glu Glu Gln Lys Leu Arg Ser Ala Gly
        115                 120                 125

Glu Leu Glu Leu Lys Phe Arg Arg Val Lys Cys Glu Tyr Pro Lys Gly
    130                 135                 140

Thr Lys Val Thr Phe His Val Glu Lys Gly Ser Asn Pro Asn Tyr Leu
145                 150                 155                 160

Ala Leu Leu Val Lys Tyr Val Asp Gly Asp Gly Asp Val Val Ala Val
                165                 170                 175

Asp Ile Lys Glu Lys Gly Lys Asp Lys Trp Ile Glu Leu Lys Glu Ser
            180                 185                 190

Trp Gly Ala Val Trp Arg Val Asp Thr Pro Asp Lys Leu Thr Gly Pro
        195                 200                 205

```
Phe Thr Val Arg Tyr Thr Thr Glu Gly Gly Thr Lys Val Glu Ala Glu
            210                 215                 220
Asp Val Ile Pro Glu Gly Trp Lys Ala Asp Thr Ala Tyr Glu Ser Lys
225                 230                 235                 240
```

<210> SEQ ID NO 35
<211> LENGTH: 240
<212> TYPE: PRT
<213> ORGANISM: Lolium perenne

<400> SEQUENCE: 35

```
Ile Ala Lys Val Pro Pro Gly Pro Asn Ile Thr Ala Glu Tyr Gly Asp
  1               5                  10                  15
Lys Trp Leu Asp Ala Lys Ser Thr Trp Tyr Gly Lys Pro Thr Gly Ala
             20                  25                  30
Gly Pro Lys Asp Asn Gly Gly Ala Cys Gly Tyr Lys Asp Val Asp Lys
         35                  40                  45
Ala Pro Phe Asn Gly Met Thr Gly Cys Gly Asn Thr Pro Ile Phe Lys
     50                  55                  60
Asp Gly Arg Gly Cys Gly Ser Cys Phe Glu Ile Lys Cys Thr Lys Pro
 65                  70                  75                  80
Glu Ser Cys Ser Gly Glu Ala Val Thr Val Thr Ile Thr Asp Asp Asn
                 85                  90                  95
Glu Glu Pro Ile Ala Pro Tyr His Phe Asp Leu Ser Gly His Ala Phe
            100                 105                 110
Gly Ser Met Ala Lys Lys Gly Glu Glu Gln Asn Val Arg Ser Ala Gly
        115                 120                 125
Glu Leu Glu Leu Gln Phe Arg Arg Val Lys Cys Lys Tyr Pro Asp Asp
    130                 135                 140
Thr Lys Pro Thr Phe His Val Glu Lys Gly Ser Asn Pro Asn Tyr Leu
145                 150                 155                 160
Ala Ile Leu Val Lys Tyr Val Asp Gly Asp Gly Asp Val Val Ala Val
                165                 170                 175
Asp Ile Lys Glu Lys Gly Lys Asp Lys Trp Ile Glu Leu Lys Glu Ser
            180                 185                 190
Trp Gly Ala Val Trp Arg Ile Asp Thr Pro Asp Lys Leu Thr Gly Pro
        195                 200                 205
Phe Thr Val Arg Tyr Thr Thr Glu Gly Gly Thr Lys Ser Glu Val Glu
    210                 215                 220
Asp Val Ile Pro Glu Gly Trp Lys Ala Asp Thr Ser Tyr Ser Ala Lys
225                 230                 235                 240
```

<210> SEQ ID NO 36
<211> LENGTH: 244
<212> TYPE: PRT
<213> ORGANISM: Cynodon dactylon

<400> SEQUENCE: 36

```
Ala Met Gly Asp Lys Pro Gly Pro Asn Ile Thr Ala Thr Tyr Gly Asp
  1               5                  10                  15
Lys Trp Leu Asp Ala Lys Ala Thr Phe Tyr Gly Ser Asp Pro Arg Gly
             20                  25                  30
Ala Ala Pro Asp Asp His Gly Gly Ala Cys Gly Tyr Lys Asp Val Asp
         35                  40                  45
Lys Ala Pro Phe Asp Gly Met Thr Gly Cys Gly Asn Glu Pro Ile Phe
     50                  55                  60
```

```
Lys Asp Gly Leu Gly Cys Gly Ser Cys Tyr Glu Ile Lys Cys Lys Glu
 65                  70                  75                  80

Pro Ala Glu Cys Ser Gly Glu Pro Val Leu Ile Lys Ile Thr Asp Lys
                 85                  90                  95

Asn Tyr Glu His Ile Ala Ala Tyr His Phe Asp Leu Ser Gly Lys Ala
                100                 105                 110

Phe Gly Ala Met Ala Lys Lys Gly Glu Glu Asp Lys Leu Arg Lys Ala
                115                 120                 125

Gly Glu Leu Met Leu Gln Phe Arg Arg Val Lys Cys Glu Tyr Pro Ser
        130                 135                 140

Asp Thr Lys Ile Thr Phe His Val Glu Lys Gly Ser Ser Pro Asn Tyr
145                 150                 155                 160

Leu Ala Leu Leu Val Lys Tyr Ala Ala Gly Asp Gly Asn Ile Val Gly
                165                 170                 175

Val Asp Ile Lys Pro Lys Gly Ser Asp Val Phe Leu Pro Met Lys Leu
                180                 185                 190

Ser Trp Gly Ala Ile Trp Arg Met Asp Pro Pro Lys Pro Leu Lys Gly
                195                 200                 205

Pro Phe Thr Ile Arg Leu Thr Ser Glu Ser Gly Gly His Val Glu Gln
        210                 215                 220

Glu Asp Val Ile Pro Glu Asp Trp Lys Pro Asp Thr Val Tyr Lys Ser
225                 230                 235                 240

Lys Ile Gln Phe

<210> SEQ ID NO 37
<211> LENGTH: 245
<212> TYPE: PRT
<213> ORGANISM: Oryza sativa

<400> SEQUENCE: 37

Gly Pro Pro Lys Val Pro Pro Gly Pro Asn Ile Thr Thr Ser Tyr Gly
  1               5                  10                  15

Asp Lys Trp Leu Glu Ala Lys Ala Thr Trp Tyr Gly Ala Pro Lys Gly
                 20                  25                  30

Ala Gly Pro Lys Asp Asn Gly Ala Cys Gly Tyr Lys Asp Val Asp
                 35                  40                  45

Lys Ala Pro Phe Leu Gly Met Asn Ser Cys Gly Asn Asp Pro Ile Phe
 50                  55                  60

Lys Asp Gly Lys Gly Cys Gly Ser Cys Phe Glu Ile Lys Cys Ser Lys
 65                  70                  75                  80

Pro Glu Ala Cys Ser Asp Lys Pro Ala Leu Ile His Val Thr Asp Met
                 85                  90                  95

Asn Asp Glu Pro Ile Ala Ala Tyr His Phe Asp Leu Ser Gly Leu Ala
                100                 105                 110

Phe Gly Ala Met Ala Lys Asp Gly Lys Asp Glu Glu Leu Arg Lys Ala
                115                 120                 125

Gly Ile Ile Asp Thr Gln Phe Arg Arg Val Lys Cys Lys Tyr Pro Ala
        130                 135                 140

Asp Thr Lys Ile Thr Phe His Ile Glu Lys Ala Ser Asn Pro Asn Tyr
145                 150                 155                 160

Leu Ala Leu Leu Val Lys Tyr Val Ala Gly Asp Gly Asp Val Val Glu
                165                 170                 175

Val Glu Ile Lys Glu Lys Gly Ser Glu Glu Trp Lys Ala Leu Lys Glu
                180                 185                 190

Ser Trp Gly Ala Ile Trp Arg Ile Asp Thr Pro Lys Pro Leu Lys Gly
```

```
                    195                 200                 205
Pro Phe Ser Val Arg Val Thr Thr Glu Gly Gly Glu Lys Ile Ile Ala
210                 215                 220

Glu Asp Ala Ile Pro Asp Gly Trp Lys Ala Asp Ser Val Tyr Lys Ser
225                 230                 235                 240

Asn Val Gln Ala Lys
                245

<210> SEQ ID NO 38
<211> LENGTH: 240
<212> TYPE: PRT
<213> ORGANISM: Phalaris aquatica

<400> SEQUENCE: 38

Ile Ala Lys Val Pro Gly Pro Asn Ile Thr Ala Glu Tyr Gly Asp
  1               5                  10                  15

Lys Trp Leu Asp Ala Lys Ser Thr Trp Tyr Gly Lys Pro Thr Gly Ala
                 20                  25                  30

Gly Pro Lys Asp Asn Gly Gly Ala Cys Gly Tyr Lys Asp Val Asp Lys
             35                  40                  45

Ala Pro Phe Asn Gly Met Thr Gly Cys Gly Asn Thr Pro Ile Phe Lys
 50                  55                  60

Asp Gly Arg Gly Cys Gly Ser Cys Phe Glu Leu Lys Cys Ser Lys Pro
65                  70                  75                  80

Glu Ser Cys Ser Gly Glu Pro Ile Thr Val His Ile Thr Asp Asp Asn
                85                  90                  95

Glu Glu Pro Ile Ala Pro Tyr His Phe Asp Leu Ser Gly His Ala Phe
            100                 105                 110

Gly Ser Met Ala Lys Lys Gly Glu Glu Glu Asn Val Arg Gly Ala Gly
        115                 120                 125

Glu Leu Glu Leu Gln Phe Arg Arg Val Lys Cys Lys Tyr Pro Asp Gly
    130                 135                 140

Thr Lys Pro Thr Phe His Val Glu Lys Gly Ser Asn Pro Asn Tyr Leu
145                 150                 155                 160

Ala Leu Leu Val Lys Tyr Val Asp Gly Asp Gly Asp Val Val Ala Val
                165                 170                 175

Asp Ile Lys Glu Lys Gly Lys Asp Lys Trp Ile Glu Leu Lys Glu Ser
            180                 185                 190

Trp Gly Ala Ile Trp Arg Ile Asp Thr Pro Asp Lys Leu Thr Gly Pro
        195                 200                 205

Phe Thr Val Arg Tyr Thr Thr Glu Gly Gly Thr Lys Ala Glu Phe Glu
210                 215                 220

Asp Val Ile Pro Glu Gly Trp Lys Ala Asp Thr His Asp Ala Ser Lys
225                 230                 235                 240

<210> SEQ ID NO 39
<211> LENGTH: 240
<212> TYPE: PRT
<213> ORGANISM: Phleum pratense

<400> SEQUENCE: 39

Ile Pro Lys Val Pro Gly Pro Asn Ile Thr Ala Thr Tyr Gly Asp
  1               5                  10                  15

Lys Trp Leu Asp Ala Lys Ser Thr Trp Tyr Gly Lys Pro Thr Ala Ala
                 20                  25                  30

Gly Pro Lys Asp Asn Gly Gly Ala Ser Gly Tyr Lys Asp Val Asp Lys
             35                  40                  45
```

```
Pro Pro Phe Ser Gly Met Thr Gly Ser Gly Asn Thr Pro Ile Phe Lys
        50                  55                  60

Ser Gly Arg Gly Ser Gly Ser Ser Phe Glu Ile Lys Ser Thr Lys Pro
 65                  70                  75                  80

Glu Ala Ser Ser Gly Glu Pro Val Val Val His Ile Thr Asp Asp Asn
                     85                  90                  95

Glu Glu Pro Ile Ala Ala Tyr His Phe Asp Leu Ser Gly Ile Ala Phe
                100                 105                 110

Gly Ser Met Ala Lys Lys Gly Asp Glu Gln Lys Leu Arg Ser Ala Gly
            115                 120                 125

Glu Val Glu Ile Gln Phe Arg Arg Val Lys Ser Lys Tyr Pro Glu Gly
130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
                165                 170                 175

Asp Ile Lys Glu Lys Gly Lys Asp Lys Trp Ile Ala Leu Lys Glu Ser
                180                 185                 190

Trp Gly Ala Ile Trp Arg Ile Asp Thr Pro Glu Val Leu Lys Gly Pro
                195                 200                 205

Phe Thr Val Arg Tyr Thr Thr Glu Gly Gly Thr Lys Gly Glu Ala Lys
210                 215                 220

Asp Val Ile Pro Glu Gly Trp Lys Ala Asp Thr Ala Tyr Glu Ser Lys
225                 230                 235                 240

<210> SEQ ID NO 40
<211> LENGTH: 232
<212> TYPE: PRT
<213> ORGANISM: Phleum pratense

<400> SEQUENCE: 40

Ile Pro Lys Val Pro Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Ala Ala
             20                  25                  30

Gly Pro Lys Asp Asn Gly Gly Ala Ser Gly Tyr Lys Asp Val Asp Lys
         35                  40                  45

Pro Pro Phe Ser Gly Met Thr Gly Ser Gly Asn Thr Pro Ile Phe Lys
     50                  55                  60

Ser Gly Arg Gly Ser Gly Ser Ser Phe Glu Ile Lys Ser Thr Lys Pro
 65                  70                  75                  80

Glu Ala Ser Ser Gly Glu Pro Val Val Val His Ile Thr Asp Asp Asn
                 85                  90                  95

Glu Glu Pro Ile Ala Ala Tyr His Phe Asp Leu Ser Gly Ile Ala Phe
            100                 105                 110

Gly Ser Met Ala Lys Lys Gly Asp Glu Gln Lys Leu Arg Ser Ala Gly
        115                 120                 125

Glu Val Glu Ile Gln Phe Arg Arg Val Lys Ser Lys Tyr Pro Glu Gly
130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
                165                 170                 175

Asp Ile Lys Glu Lys Gly Lys Asp Lys Trp Ile Ala Leu Lys Glu Ser
            180                 185                 190
```

-continued

```
Trp Gly Ala Ile Trp Arg Ile Asp Thr Pro Glu Val Leu Lys Gly Pro
        195                 200                 205

Phe Thr Val Arg Gly Glu Ala Lys Asp Val Ile Pro Glu Gly Trp Lys
        210                 215                 220

Ala Asp Thr Ala Tyr Glu Ser Lys
225                 230

<210> SEQ ID NO 41
<211> LENGTH: 221
<212> TYPE: PRT
<213> ORGANISM: Phleum pratense

<400> SEQUENCE: 41

Gly Pro Asn Ile Thr Ala Thr Tyr Gly Asp Lys Trp Leu Asp Ala Lys
1               5                   10                  15

Ser Thr Trp Tyr Gly Lys Pro Thr Ala Ala Gly Pro Lys Asp Asn Gly
                20                  25                  30

Gly Ala Ser Gly Tyr Lys Asp Val Asp Lys Pro Pro Phe Ser Gly Met
            35                  40                  45

Thr Gly Ser Gly Asn Thr Pro Ile Phe Lys Ser Gly Arg Gly Ser Gly
    50                  55                  60

Ser Ser Phe Glu Ile Lys Ser Thr Lys Pro Glu Ala Ser Ser Gly Glu
65                  70                  75                  80

Pro Val Val Val His Ile Thr Asp Asp Asn Glu Glu Pro Ile Ala Ala
                85                  90                  95

Tyr His Phe Asp Leu Ser Gly Ile Ala Phe Gly Ser Asp Glu Gln Lys
                100                 105                 110

Leu Arg Ser Ala Gly Glu Val Glu Ile Gln Phe Arg Arg Val Lys Ser
            115                 120                 125

Lys Tyr Pro Glu Gly Thr Lys Val Thr Phe His Val Glu Lys Gly Ser
    130                 135                 140

Asn Pro Asn Tyr Leu Ala Leu Leu Val Lys Phe Val Ala Gly Asp Gly
145                 150                 155                 160

Asp Val Val Ala Val Asp Ile Lys Glu Lys Gly Lys Asp Lys Trp Ile
                165                 170                 175

Ala Leu Lys Glu Ser Trp Gly Ala Ile Trp Arg Ile Asp Thr Pro Glu
            180                 185                 190

Val Leu Lys Gly Pro Phe Thr Val Arg Gly Glu Ala Lys Asp Val Ile
    195                 200                 205

Pro Glu Gly Trp Lys Ala Asp Thr Ala Tyr Glu Ser Lys
    210                 215                 220
```

We claim:

1. A recombinant variant of *Phleum pratense* Phl p 1 polypeptide, comprising substitution or deletion of cysteines at amino acid positions 41, 57, 69, 72, 77, 83 and 139 in SEQ ID NO: 2.

2. The recombinant variant of *Phleum pratense* Phl p 1 polypeptide according to claim 1, comprising substitution of cysteines at amino acid positions 41, 57, 69, 72, 77, 83 and 139 in SEQ ID NO: 2 by another amino acid.

3. The recombinant variant of *Phleum pratense* Phl p 1 polypeptide according to claim 1, which comprises the sequence set forth in SEQ ID NO: 4.

4. A medicament comprising the polypeptide variant according to claim 1 and a carrier.

5. A pharmaceutical composition comprising the polypeptide variant according to claim 1 and an adjuvant.

6. A method for the immunotherapy of allergies triggered by group 1 allergens from Poaceae species, comprising administering to a subject in need thereof the recombinant variant of *Phleum pratense* Phl p 1 polypeptide according to claim 1.

7. A method for the immunotherapy of allergies triggered by group 1 allergens from Poaceae species, comprising administering to a subject in need thereof the pharmaceutical composition according to claim 5.

8. A process for the preparation of the polypeptide variant according to claim 1 comprising culturing a host organism which comprises a polynucleotide that encodes said polypeptide variant under conditions sufficient to express said polypeptide variant and isolating said polypeptide variant from the culture.

9. A variant of *Phleum pratense* Phl p 1 polypeptide comprising deletion of at least one region or a combination of regions corresponding to amino acids 1-6, 1-30, 92-104, 115-119, 175-185 and 213-220 in the mature Phl p 1 polypeptide sequence set forth in SEQ ID NO: 2.

10. The variant of *Phleum pratense* Phl p 1 polypeptide according to claim 9, comprising deletion of amino acids 213-220 in the mature Phl p 1 polypeptide sequence set forth in SEQ ID NO: 2.

11. The variant of *Phleum pratense* Phl p 1 polypeptide according to claim 9, comprising deletion of amino acids 1-6, 115-119 and 213-220 in the mature Phl p 1 polypeptide sequence set forth in SEQ ID NO: 2.

12. The variant of *Phleum pratense* Phl p 1 polypeptide according to claim 9, which additionally comprises a deletion or a substitution of cysteines at amino acid positions 41, 57, 69, 72, 77, 83 and 139 in the mature Phl p 1 polypeptide sequence set forth in SEQ ID NO: 2.

13. A recombinant variant of *Phleum pratense* Phl p 1 polypeptide comprising deletion of at least one region or a combination of regions corresponding to amino acids 1-6, 1-30, 92-104, 115-119, 175-185 and 213-220 of the primary sequence of the mature Phl p 1 polypeptide sequence set forth in SEQ ID NO: 2 and further comprising substitution of cysteines at amino acid positions 41, 57, 69, 72, 77, 83 and 139 in said SEQ ID NO: 2.

14. The variant of *Phleum pratense* Phl p 1 polypeptide according to claim 13 which comprises the sequence set forth in SEQ ID NO: 16.

15. The variant of *Phleum pratense* Phl p 1 polypeptide according to claim 13, which comprises the sequence set forth in SEQ ID NO: 18.

16. A deletion variant of *Phleum pratense* polypeptide, which comprises the polypeptide sequence set forth in SEQ ID NO: 6, SEQ ID NO; 8, SEQ ID NO: 10, SEQ ID NO: 12, SEQ ID NO: 14, SEQ ID NO: 16 or SEQ ID NO: 18.

\* \* \* \* \*

UNITED STATES PATENT AND TRADEMARK OFFICE
CERTIFICATE OF CORRECTION

| | | |
|---|---|---|
| PATENT NO. | : 8,263,090 B2 | Page 1 of 1 |
| APPLICATION NO. | : 11/572370 | |
| DATED | : September 11, 2012 | |
| INVENTOR(S) | : Fiebig et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 645 days.

Signed and Sealed this
Twenty-ninth Day of December, 2015

Michelle K. Lee
*Director of the United States Patent and Trademark Office*